US009700653B2

(12) United States Patent
Venkatraman et al.

(10) Patent No.: US 9,700,653 B2
(45) Date of Patent: Jul. 11, 2017

(54) METHOD FOR PREPARING A PATTERNED SUBSTRATE AND USE THEREOF IN IMPLANTS FOR TISSUE ENGINEERING

(71) Applicant: Nanyang Technological University, Singapore (SG)

(72) Inventors: Subramanian Venkatraman, Singapore (SG); Scott Alexander Irvine, Singapore (SG); Chee Kai Chua, Singapore (SG); Animesh Agrawal, Singapore (SG); Jia An, Singapore (SG)

(73) Assignee: Nanyang Technological University, Singapore (SG)

( * ) Notice: Subject to any disclaimer, the term of this patent is extended or adjusted under 35 U.S.C. 154(b) by 274 days.

(21) Appl. No.: 14/332,059

(22) Filed: Jul. 15, 2014

(65) Prior Publication Data

US 2015/0024493 A1    Jan. 22, 2015

Related U.S. Application Data

(60) Provisional application No. 61/846,773, filed on Jul. 16, 2013, provisional application No. 61/846,761, filed on Jul. 16, 2013.

(51) Int. Cl.
| | |
|---|---|
| *A61L 27/18* | (2006.01) |
| *A61L 27/34* | (2006.01) |
| *A61L 27/38* | (2006.01) |
| *A61L 27/50* | (2006.01) |
| *A61L 27/58* | (2006.01) |

(52) U.S. Cl.
CPC ............. *A61L 27/50* (2013.01); *A61L 27/18* (2013.01); *A61L 27/34* (2013.01); *A61L 27/3804* (2013.01); *A61L 27/58* (2013.01)

(58) Field of Classification Search
CPC .. A61K 2300/00; A61K 31/337; A61K 31/70; A61K 31/7088; A61K 9/0021; A61K 31/00; A61K 33/00; A61K 38/38; A61K 38/4833; A61K 38/4886; A61K 39/00; A61K 41/0004; A61K 45/06; A61K 9/0019; A61K 9/007; A61K 9/00; A61L 27/18; A61L 27/34; A61L 27/3804; A61L 27/50; A61L 27/58; C08L 67/04; C08L 89/06
See application file for complete search history.

(56) References Cited

U.S. PATENT DOCUMENTS

| | | | |
|---|---|---|---|
| 7,338,517 B2 | 3/2008 | Yost et al. | |
| 7,579,189 B2 | 8/2009 | Freyman et al. | |
| 2013/0018454 A1 | 1/2013 | Lelkes et al. | |
| 2013/0052254 A1* | 2/2013 | Arinzeh | A61L 27/16 424/443 |

FOREIGN PATENT DOCUMENTS

| | | |
|---|---|---|
| WO | 2009/103012 A1 | 8/2009 |
| WO | 2012/057706 A1 | 5/2012 |

OTHER PUBLICATIONS

Dahl et al., "Readily Available Tissue-Engineered Vascular Grafts," *Sci Transl Med* 3(68), Feb. 2, 2011, 13 pages.
Gwyther et al., *Regenerating the Heart*, Cohen, I.S. and Gaudette, G.R. (eds.), Springer Science+Business Media, LLC, 2011, "Regenerating Blood Vessels," pp. 393-402.
Kai et al., "Guided orientation of cardiomyocytes on electrospun aligned nanofibers for cardiac tissue engineering," *Journal of Biomedical Materials Research B: Applied Biomaterials* 98B(2):379-386, Aug. 2011.
Kong et al., "Characterization and degradation of elastomeric four-armed star copolymers based on caprolactone and L-lactide," *Journal of Biomedical Materials Research A* 100A(12):3436-3445, Dec. 2012.
Konig et al., "Mechanical properties of completely autologous human tissue engineered blood vessels compared to human saphenous vein and mammary artery," *Biomaterials* 30:1542-1550, 2009.
L'Heureux et al., "Human tissue-engineered blood vessels for adult arterial revascularization," *Nature Medicine* 12(3):361-365, Mar. 2006.
Li et al., "Direct laser machining-induced topographic pattern promotes up-regulation of myogenic markers in human mesenchymal stem cells," *Acta Biomaterialia* 8:531-539, 2012.
Lipik et al., "Thermoplastic biodegradable elastomers based on ε-caprolactone and L-lactide block co-polymers: A new synthetic approach," *Acta Biomaterialia* 6:4261-4270, 2010.
Sell et al., "Electrospun polydioxanone-elastin blends: potential for bioresorbable vascular grafts," *Biomedical Materials* 1:72-80, 2006.
Tay et al., "Bio-inspired Micropatterned Platform to Steer Stem Cell Differentiation," *Small* 7(10):1416-1421, 2011.
Tay et al., "Micro- / Nano-engineered Cellular Responses for Soft Tissue Engineering and Biomedical Applications," *Small* 7(10):1361-1378, 2011.
Widjaja et al., "Triblock copolymers of ε-caprolactone, L-lactide, and trimethylene carbonate: Biodegradability and elastomeric behavior," *Journal of Biomedical Materials Research A* 99A(1):38-46, Oct. 2011.

(Continued)

*Primary Examiner* — Debbie K Ware
(74) *Attorney, Agent, or Firm* — Seed IP Law Group LLP

(57) ABSTRACT

A method for preparing a patterned substrate is provided. The method includes melt-spinning at least one biocompatible polymer to form fibers; collecting the fibers on a substrate such that the fibers are aligned on the substrate; and applying a binding agent to the aligned fibers to bond the fibers into the aligned arrangement to obtain the patterned substrate in form of an aligned fiber mat. Use of the patterned substrate in an implant for tissue engineering is also provided.

20 Claims, 22 Drawing Sheets

(56) References Cited

OTHER PUBLICATIONS

Xu et al., "Aligned biodegradable nanofibrous structure: a potential scaffold for blood vessel engineering," *Biomaterials* 25:877-886, 2004.

* cited by examiner (A)

(B)

| Samples | No. of cells before centrifuge | No. of cells after centrifuge | Cell loss (%) |
|---|---|---|---|
| Control | 47953 | 22998 | 52 |
| NaOH treated PCL film | 53304 | 44767 | 16 |
| Absorbed gelatin on NaOH treated PCL film | 60682 | 42129 | 30.6 |
| Gelatin crosslinked on NaOH treated PCL film | 82378 | 73088 | 11.3 |

(A)

A.

B.

C.

D.

(A)

(B)

(C)

(A)

(B)

(A)

(B)

Hydrogel crosslinked inside pluronic coated glass tube

Crosslinked hydrogel readily released from pluronic coated glass tube, after incubation at 4°C

A.  B.  C.

A.
B.
C.
D.

(A)

(B)

(C)

(A)

(B)

(C)

(D)

(E)

(F)

(A)

(B)

(A)

(B)

(C)

(D)

(A)

(B)

(C)

(D)

METHOD FOR PREPARING A PATTERNED SUBSTRATE AND USE THEREOF IN IMPLANTS FOR TISSUE ENGINEERING

CROSS-REFERENCE TO RELATED APPLICATIONS

This application claims the benefit of priority of U.S. provisional application No. 61/846,773 filed on 16 Jul. 2013 and U.S. provisional application No. 61/846,761 filed on 16 Jul. 2013, the content of which are incorporated herein by reference in their entirety for all purposes.

TECHNICAL FIELD

Various embodiments relate generally to a method of preparing a patterned substrate and use thereof in manufacture of implants for tissue engineering.

BACKGROUND

Understanding and manipulation of cell-substrate interactions have increased in importance as research in implantable biomaterial advances. One area of interest relates to production of a more natural-like construct that is able to recruit and control patterning of functional cells to mimic natural tissue organization.

Aligned orientation of cells on extracellular matrix (ECM), for example, plays an important role in tissues such as corneal stroma, tendons, bones, skeletal muscle and vasculature.

In particular, development of small diameter vascular prostheses for arterial disease remains problematic due to poor compliance and vasoactivity for small diameter prostheses. For example, the implanted prostheses tend to occlude fairly quickly, compared to saphenous vein grafts. As such, smaller arteries (2 mm to 5 mm) are currently only treated with angioplasty and/or stenting. Other reasons for failure of small blood vessel prostheses in vivo include: (i) compliance mismatch between prosthesis and blood vessel, which leads to anastomic hyperplasia; and (ii) acute and delayed thrombosis due to material used.

Use of two predominant cell types within blood vessels, namely fibroblasts and vascular smooth muscle cells (VSMCs), may functionally benefit cell-seeded prosthesis if they are used in an aligned orientation.

Fibroblasts produce extracellular matrix (ECM) such as collagen fibrils and elastin that confer blood vessels much of their mechanical and structural properties. In the context of a vascular prosthesis, it is beneficial to align growth of cells, as they may in turn control pattern of ECM deposition. As such ECM may gradually replace medical prosthesis constructs formed of a biodegradable material, distribution of the cells and methods of influencing their growth are of importance.

VSMCs represent another predominant cell type within blood vessels. They are integral to vascular functioning through regulation of vessel tone and lumen diameter. Interestingly, these cells exist as two very distinct phenotypes: (i) contractile VSMCs, characterized by their spindle shapes and abundance of alpha smooth muscle actin ($\alpha$-SMA); and (ii) synthetic VSMCs, recognizable by their rhomboid shapes and reduced $\alpha$-SMA.

Contractile VSMCs allow changes that mediate blood pressure by altering vessels luminal diameter. Secretary phenotypes, on the other hand, are associated with tissue remodeling, inflammation and proliferation, and are central to pathology of neointimal hyperplasia and artery bypass failure.

There is plasticity between the contractile and phenotype states as they are not differentiation end-points. During culturing of VSMCs, freshly seeded cells exist primarily in the contractile state. Over time, the population shifts towards predominantly secretory phenotypes. Aligned orientation of VSMCs within engineered parallel grooves, however, has been found to preserve the contractile state over extended periods of culturing. Preservation of phenotype is important, as only VSMCs in the contractile state are beneficial in fabricating cellularised tissue engineered blood vessel (TEBV). Furthermore, the cells must be circumferentially orientated to direct their function.

To date, no tissue-engineered construct or fully-synthetic vascular prosthesis has been approved for use in small-diameter blood vessel replacement.

Apart from the above-mentioned, mesenchymal stem cells may be a potential cell source in cardiac regeneration for use in necrotic areas of heart tissue. The mesenchymal stem cells may differentiate towards the cardiomyocyte lineage to restore tissue function. Stem cells may be expanded and cultured ex vivo, whereas cardiomyocytes are terminally differentiated. The concept has been expanded to creating a heart patch scaffold colonized with functioning myocytes for the replacement of infracted heart tissue. The differentiation of mesenchymal stem cell towards cardiomyocytes may be aided by surface cues incorporated into the scaffold. In particular, linear patterning using fibers and cut grooves may promote differentiation of mesenchymal stem cells to cardiomyocytes.

In view of the above, there remains a need for a method to fabricate a patterned surface for cell growth, including implants having such a patterned surface, that overcomes or at least alleviates one or more of the above-mentioned problems.

SUMMARY

In a first aspect, a method for preparing a patterned substrate is provided. The method comprises:
  a) melt-spinning at least one biocompatible polymer to form fibers;
  b) collecting the fibers on a substrate such that the fibers are aligned on the substrate; and
  c) applying a binding agent to the aligned fibers to bond the fibers into the aligned arrangement to obtain the patterned substrate in form of an aligned fiber mat.

In a second aspect, a method for forming an implant for tissue engineering is provided. The method comprises
  a) providing a patterned substrate prepared by a method according to the first aspect;
  b) applying one or more species of living cells to the patterned substrate;
  c) incubating the patterned substrate comprising the one or more species of living cells under conditions which allow proliferation of the one or more species of living cells; and
  d) degrading the patterned substrate to obtain the implant.

BRIEF DESCRIPTION OF THE DRAWINGS

Various embodiments will be better understood with reference to the detailed description when considered in conjunction with the non-limiting examples and the accompanying drawings, in which.

DETAILED DESCRIPTION

Figure 1:
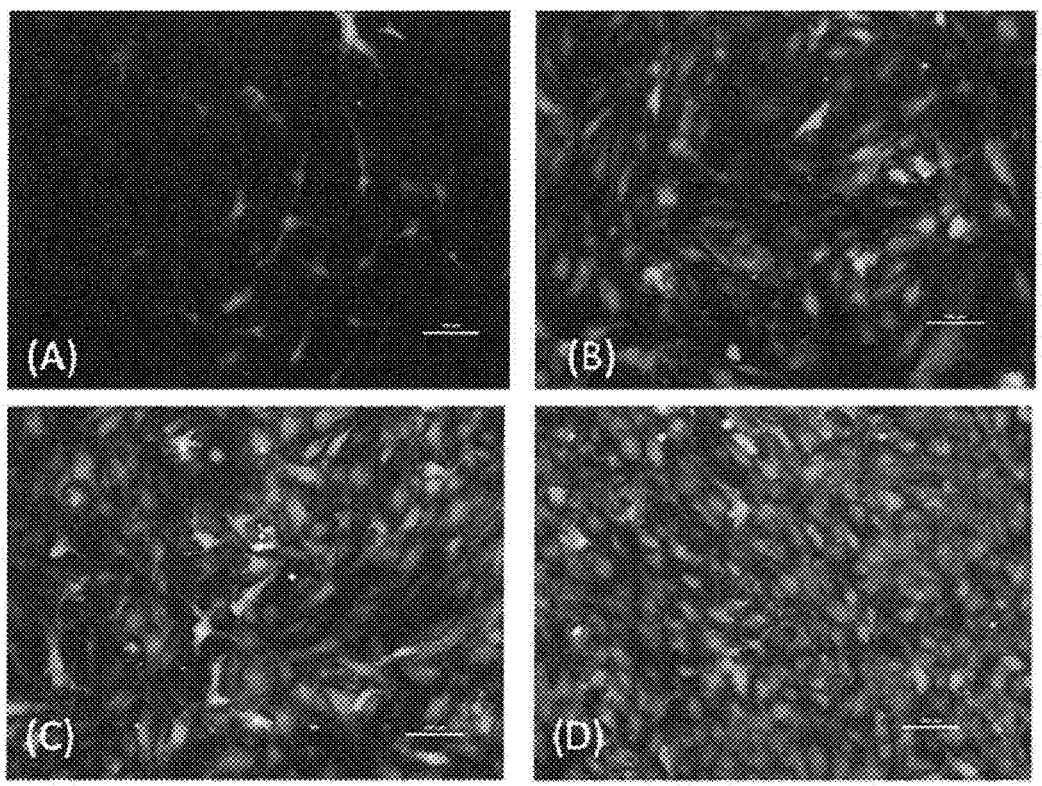
FIG. 1 shows Human Umbilical Vein Endothelial Cells (HUVECs) cell growth on polycaprolactone (PCL) films after 48 hrs of seeding on (A) control PCL film; (B) PCL film treated with 1M sodium hydroxide (NaOH) for 1 hr; (C) NaOH treated absorbed gelatin solution; and (D) crosslinked gelatin. Scale bar in the figures represents 100 µm.

In a first aspect, a method for preparing a patterned substrate is provided. The patterned substrate may be used in a myriad of applications such as implants for tissue engineering. Advantageously, use of melt-spinning to form the fibers allows greater fiber alignment than may be obtained using other types of processes. Furthermore, formation of the patterned substrate may be carried out in a simple and cost efficient manner, as expensive equipments, such as femtolaser, are not used.

As used herein, the term "patterned substrate" refers to an object having one or more patterns, which may be in the form of structures, shapes, and/or formations, on a surface of the object. The one or more patterns may be an ordered arrangement, meaning that the structures, shapes, and/or formations may form a repeating design or pattern across a surface of the patterned substrate.

The method comprises melt-spinning at least one biocompatible polymer to form fibers. The term "biocompatible" as used herein refers to substances that are not toxic to cells. For example, a substance may be considered to be biocompatible if, upon contact of the substance with cells, there is less than or equal to about 10%, about 5%, or less than about 5% cell death.

The at least one biocompatible polymer may be a biodegradable polymer or a biostable polymer, preferably a biostable polymer.

The term "biodegradable" refers generally to a substance which may be broken down by microorganisms, or which spontaneously breaks down over a relatively short time (within 2 to 15 months) when exposed to environmental conditions commonly found in nature. As used herein, the term "biodegradable" also refers to substances that may be broken down by microorganisms under physiological conditions, such as in an animal body.

Examples of biodegradable polymers include, but are not limited to, polymers and oligomers of glycolide, lactide, polylactic acid, polyesters of a-hydroxy acids, including lactic acid and glycolic acid, such as the poly(a-hydroxy) acids including polyglycolic acid, poly-DL-lactic, poly-L-lactic acid, and terpolymers of DL-lactide and glycolide; e-caprolactone and e-caprolactone copolymerized with polyesters; polylactones and polycaprolactones including poly(e-caprolactone), poly(δ-valerolactone) and poly (gamma-butyrolactone); polyanhydrides; polyorthoesters; other hydroxy acids; polydioxanone; and other biologically degradable polymers that are non-toxic or are present as metabolites in the body. Examples of polyaminoacids include, but are not limited to, polylysine (PLL), poly L-aspartic acid, poly L-glutamic acid, and styrene-maleic acid anhydride copolymer. Examples of derivatives of polyethylene glycol includes, but are not limited to, poly(ethylene glycol)-di-(ethylphosphatidyl(ethylene glycol)) (PEDGA), poly(ethylene glycol)-co-anhydride, poly(ethylene glycol)co-lactide, poly(ethylene glycol)-co-glycolide and poly(ethylene glycol)-co-orthoester. Examples of acrylamide polymers include, but are not limited to, polyisopropylacrylamide, and polyacrylamide. Examples of acrylate polymers include, but are not limited to, diacrylates such as polyethylene glycol diacrylate (PEGDA), oligoacrylates, methacrylates, dimethacrylates, oligomethoacrylates and PEG-oligoglycolylacrylates. Examples of carboxy alkyl cellulose include, but are not limited to, carboxymethyl cellulose and partially oxidized cellulose.

In various embodiments, the biocompatible polymer is a biostable polymer. As used herein, the term "biostable" refers to ability of the polymer to maintain stability when in contact with cells and/or bodily fluids of living animals or humans.

Examples of biostable polymers include, but are not limited to, silicones, polyurethanes, polyethylenes, polysulfones, polyisobutylene, poly-4 methyl pentene, polypropylene, polyvinylethylene, polybutylene, polydodecyl methacrylate, polyethylene terephthalate, ethylene vinyl acetate, ethylene vinyl alcohol copolymer, polyethylene oxide, combinations thereof, or copolymers thereof.

In specific embodiments, the biocompatible polymer is selected from the group consisting of elastin, collagen, polyurethane, polycaprolactone, polylactide, polyglycolic acid, mixtures thereof, and copolymers thereof.

The at least one biocompatible polymer undergoes melt-spinning to form fibers. As used herein, the term "melt-spinning" refers to a process in which molten polymers are extruded into separately formed fibers or filaments. For example, a thermoplastic polymer may be heated at a temperature higher than its melting point, such that it transforms into its molten state. The molten polymer may subsequent be fed through a spinneret or die orifices to form the fibers or filaments.

Advantageously, using a melt-spinning process, removal of secondary substances is not required, as secondary substances such as solvents are not used. This may translate into improved quality of the obtained fibers. Furthermore, use of melt-spinning allows greater fiber alignment than may be obtained using other types of process.

The method includes collecting the fibers on a substrate such that the fibers are aligned on the substrate.

The substrate may have a surface topography that is planar or non-planar. In various embodiments, the substrate may be an object having a continuous surface such as a sphere, a curved surface of a cylinder, or a curved surface of a cone. In some embodiments, the substrate may be an object having a surface that is non-continuous, such as a U-shaped fork which defines a gap between its two prongs. In specific embodiments, the substrate is a hollow tube comprising or consisting of a biocompatible polymer. For example, the substrate may be a hollow tube that is formed of a biocompatible polymer. Examples of biocompatible polymers that may be used have already been mentioned above.

In various embodiments, the hollow tube is prepared by providing a cylindrical element having a first layer comprising or consisting of a water-soluble polymer coated on a lateral surface of the cylindrical element. This may be followed by coating of a second layer comprising or consisting of a biocompatible polymer on the first layer. The tubular element having the first and the second layer coated thereon may subsequently be immersed in an aqueous solution to remove the first layer. The second layer is then separated from the tubular element to obtain the hollow tube.

The first layer comprising or consisting of a water-soluble polymer coated on a lateral surface of the cylindrical element may be formed using any suitable deposition method, such as dip-coating, spray coating, painting, sputtering, self assembly, or by immersing the cylindrical element in a solution containing the first polymer.

In various embodiments, providing a cylindrical element having a first layer comprising or consisting of a water-soluble polymer coated on a lateral surface of the cylindrical element comprises dip-coating the cylindrical element in a liquid reagent comprising the water-soluble polymer.

Generally, any water-soluble polymer that is able to at least substantially dissolve in an aqueous solution may be used. Examples of water-soluble polymer include polyvinyl alcohol, polycarboxylate, sulfonated carboxylate, polyethylene glycol, polyethylene oxide polysulfonate, polyvinylpyrrolidone, combinations thereof, and copolymers thereof. In specific embodiments, the water-soluble comprises or consists of polyvinyl alcohol.

The first layer containing the water-soluble polymer may have a thickness that is sufficiently thin to provide ease of dissolution of the water-soluble polymer in a subsequent step. For example, the first layer may have a thickness of about 10 µm to about 200 µm, such as about 10 µm to about 100 µm, or about 10 µm to about 50 µm.

The method in various embodiments includes coating a second layer comprising or consisting of a biocompatible polymer on the first layer. Coating of the second layer may be carried out using any suitable deposition methods, examples of which have been provided above. Before coating of the second layer on the first layer, the first layer that is coated on the cylindrical element may be dried, for example, under ambient conditions or under an air draft.

In various embodiments, coating a second layer comprising or consisting of a biocompatible polymer on the first layer is carried out by dip-coating the cylindrical element having the first layer coated thereon in a liquid reagent comprising the biocompatible polymer dissolved in an organic solvent. Examples of biocompatible polymers that may be used have already been mentioned above.

The organic solvent used may depend on the biocompatible polymer that is used. Generally, the organic solvent is able to at least substantially dissolve the biocompatible polymer, while not reacting with and/or dissolving the first polymer. In various embodiments, the organic solvent comprises or consists of chloroform.

Following coating of the second layer, it may be allowed to dry. The cylindrical element having the first and the second layer coated thereon may subsequently be immersed in an aqueous solution to remove the first layer. Examples of aqueous solution include, but are not limited to, a buffer solution such as phosphate buffered saline, and water. In various embodiments, the aqueous solution is water.

In various embodiments, solubility of the polymer in the second layer in the aqueous solution is lower than the solubility of the polymer in the first layer in the aqueous solution, such that when the cylindrical element having the first and the second layer coated thereon is immersed in the aqueous solution, a substantial portion of or all of the polymer in the second layer remains intact. Conversely, the first layer comprising or consisting of a water-soluble polymer coated thereon may at least substantially dissolve in the aqueous solution to allow easy separation of the second layer from the cylindrical element to obtain the hollow tube.

In embodiments where the intended application of the patterned substrate involves cells growth or culturing, for example, an inner surface of the hollow tube may be subjected to one or more surface treatments to increase surface wettability and/or to promote cell proliferation and coverage of the cells on the treated surface.

For example, an inner surface of the hollow tube may be treated with an alkaline solution to increase surface wettability of the surface. Examples of alkaline solution include potassium hydroxide, sodium hydroxide, and/or ammonium hydroxide. In preferred embodiments, the alkaline solution is sodium hydroxide.

Besides treating inner surface of the hollow tube with an alkaline solution, the inner surface may be further treated with at least one of gelatin and collagen. The at least one of gelatin and collagen may be immobilized on the inner surface of the hollow tube by carbodiimide crosslinking. As mentioned above, treatment of the hollow tube with the alkaline solution, and the gelatin and/or collagen may promote cell proliferation and coverage of the cells on the treated surface.

Advantageously, a method disclosed herein allows formation of blood vessel replacements of small diameter. Accordingly, the hollow tube may have a diameter in the range of about 2 mm to about 5 mm, such as about 2 mm to about 4 mm, about 2 mm to about 3 mm, about 3 mm to about 5 mm, about 4 mm to about 5 mm, or about 3 mm to about 4 mm.

As mentioned above, the fibers that are formed by melt-spinning at least one biocompatible polymer are collected on a substrate such that the fibers are aligned on the substrate.

The fibers may be collected on a surface of a substrate such that the fibers are aligned on the substrate. In embodiments in which surface of a substrate defines a gap, such as that of a U-shaped fork mentioned above, the fibers may be collected on the substrate such that they span across the gap while being aligned on the substrate.

In various embodiments, collecting the fibers on a substrate comprises rotating the substrate such that the fibers are collected circumferentially around the substrate. For example, when the substrate is cylindrical or conical in shape, the substrate may be rotated such that the fibers are collected circumferentially around and on a lateral surface of the substrate. By moving the substrate in a lateral direction relative to the site at which the fibers are deposited on the substrate, for example, the fibers may be deposited such that they are positioned in an aligned arrangement on the substrate in form of an aligned fiber mat.

In various embodiments, the fibers are aligned to define micro grooves or nano grooves between the fibers on the substrate. The terms "micro" and "nano" refer respectively to a measure of the physical dimension that may be used to define the size of the grooves, for example, at least one of length, height and width, in units ranging from several nanometers (for nano grooves) to several micrometers (for micro grooves).

For example, a micro groove generally refers to a groove having at least one physical dimension (such as length, height or width) that is more than about 100 nm, such as about 200 nm, 300 nm, 400 nm, 500 nm, 600 nm, 700 nm, 800 nm, 900 nm, 1 µm, 2 µm, 5 µm or 10 µm. A nano groove, on the other hand, generally refers to a groove having at least one physical dimension that is less than or equal to about 100 nm, such as about 1 nm, 5 nm, 10 nm, 20 nm, 30 nm, 40 nm, 50 nm, 60 nm, 70 nm, 80 nm, 90 nm, or 100 nm.

The diameter of each fiber may be about 10 µm. Advantageously, fibers of this dimension allow cell interaction to take place across the fibers, as overlarge groove walls of extended intervals between the grooves may prevent such interaction from taking place. Accordingly, the aligned fibers may form alternating protrusions and grooves, wherein the alternating protrusions and grooves are arranged at least substantially parallel to one another. For example, the protrusion may have a height of in the range of about 1 µm to about 10 µm, such as about 1 µm to about 8 µm, or about 1 µm to about 5 µm.

Depending on the cells or tissues to be cultivated, for example, it is not necessary that each protrusion or groove that is present on the substrate have the same dimension or are spaced equally apart on the substrate. Advantageously, design of protrusions and grooves on the patterned substrate, such as size and shape of the fibers and inter-fiber distance, may be tailored to meet requirements of intended applications.

The method comprises applying a binding agent to the aligned fibers to bond the fibers into the aligned arrangement to obtain the patterned substrate in form of an aligned fiber mat.

As used herein, the term "binding agent" refers to a substance that may be used to improve adhesion between two surfaces. For example, the binding agent may be applied to a surface of the aligned fibers so as to secure or to hold the fibers together in the aligned arrangement. In so doing, a patterned substrate in the form of an aligned fiber mat may be obtained. Further, depending on the way in which the binding agent is applied, for example, the fibers may or may not be attached to the underlying substrate.

In various embodiments, the binding agent is selected from the group consisting of gel-forming polysaccharides or proteins polypeptides, alginate, glycosaminoglycans, hyaluronate, collagen, chitosan, gelatin, dopamine, and mixtures thereof.

In embodiments wherein the biocompatible polymer of the fibers comprises or consists of a copolymer of polycaprolactone and polylactide, whereby polylactide in the copolymers may be present in the range of about 50 wt % to about 80 wt % of the copolymer, it has been surprisingly found by the inventors that gelatin is preferred for use as the binding agent, as chitosan renders the fibers stiff upon drying.

In various embodiments, the patterned substrate comprises or consists essentially of fibers which are arranged at least substantially parallel to one another. As mentioned above, the fibers are aligned such that micro grooves or nano grooves are formed between the fibers on the substrate. By applying a binding agent to a surface of the aligned fibers, each of the fibers may be bonded to a neighboring fiber to form a patterned substrate in the form of an aligned fiber mat.

The patterned substrate disclosed herein may be used to grow or culture cells or tissues that are at least substantially aligned with the patterned surface of the patterned substrate. As used herein, the term "align" refers to growth and orienting of cells in one or more general directions defined by the patterns present on the patterned substrate such that the cells arrange or fall into position according to the patterns on the surface of the patterned substrate.

For example, in embodiments in which the patterned substrate comprises or consists essentially of fibers which are arranged at least substantially parallel to one another, the cells may orient themselves such that the long axis of the cells are at least substantially parallel to the fibers. In various embodiments, the cells or tissues that are grown on the patterned surface of the patterned substrate are substantially aligned with the fibers.

Besides a planar configuration, the patterned substrate formed using a method disclosed herein may also have a shape or configuration that more closely mimics tissue complexity, and which is more clinically relevant. In various embodiments, the patterned substrate may be used for making three dimensional scaffolds or implants.

Accordingly, in a second aspect, a method for forming an implant for tissue engineering is provided. The method includes providing a patterned substrate prepared by a method according to the first aspect, and applying one or more species of living cells to the patterned substrate.

The term "living cell" refers to any cell that is capable of cell division or contains a nucleus. A "living cell" also refers to a cell that has active metabolic machinery (e.g. mitochondria). The term "species of living cells" as used herein refers generally to cells from different differentiation lineages and phenotypes, though it may also refer to different types of living cells. The living cells may be eukaryotic cells, prokaryotic cells or archaea.

As used herein, the term "eukaryotic cell" refers to any animal or plant cell having a definitive nucleus. Eukaryotic cells of animals include cells of vertebrates such as mammals, and cells of invertebrates such as insects. Examples of eukaryotic cells of plants include yeast cells, and algae cells. Eukaryotic cells may also comprise antibody producing cells, such as hybridoma. The term "prokaryotic cell" refers to a cell of a prokaryotic organism that lacks a definitive nucleus. Examples of prokaryotic cells may include, but are not limited to, the genus *Escherichia, Bacillus* or *Lactococcus*. Some examples of prokaryotic cell species from these genera are *Escherichia coli, Bacillus subtilis* or *Lactococcus lactis*. The term "archaea" refers to a group of single-celled microorganisms which has no cell nucleus or any other organelles within their cells.

The eukaryotic cell may be an anchorage dependent cell. An anchorage dependent cell refers to any cell which will grow and multiply when attached to a solid support material, and are not able to grow when present in a suspension. In some embodiments, the anchorage dependent cell may be a mammalian cell.

A mammalian cell refers to any cell that is derived from a mammal Examples of mammals include, but are not limited to, a rat, a mouse, a rabbit, a guinea pig, a squirrel, a hamster, a hedgehog, a platypus, an American pika, an armadillo, a dog, a lemur, a goat, a pig, an opossum, a horse, an elephant, a bat, a woodchuck, an orang-utan, a rhesus monkey, a woolly monkey, a macaque, a chimpanzee, a tamarin (*saguinus oedipus*), a marmoset or a human. The cells may for instance be cells of a tissue, such as an organ or a portion thereof. A mammalian cell may include a mammalian cell line. In one embodiment, the mammalian cell may be a human cell. Examples of a human cell include, but are not limited to, an osteogenic cell, a fibroblast, an epidermal cell, an adipocyte, a neural cell, an endothelial cell, an epithelial cell, a keratinocyte, a hepatocyte, a myocyte, a cardiomyocyte, a cell from joint ligament, a cell from the nucleus pulposis, a HEK 293 cell and PER.C6® cell.

An osteogenic cell refers to an osteoblast or a progenitor osteoblast cell, which gives rise to a bone tissue. A fibroblast is a spindle shaped cell which can rapidly replicate and synthesize a fibrous matrix composed of a variety of extracellular matrix molecules including Type I Collagen, and which can be found in skin. An epidermal cell refers to a cell of the epidermis, wherein the epidermis is the outer layer of skin and is composed of four types of cells, i.e. keratinocyte, melanocyte, Langerhans cell, and Merkel cell. The term "adipocyte" refers to a cell existing in or derived from fat tissue which is terminally differentiated. It is also known as a lipocyte or fat cell, and specializes in storing energy as fat. In their differentiated state, adipocytes assume a rounded morphology associated with cytoskeletal changes and loss of mobility. Neural cells refer to cells of the nervous system and in particular of the brain. Examples of neural cells include, but are not limited to, neurones, astrocytes and oligodendrocytes. Endothelial cells refer to a thin, flattened cell, of which a layer of the cells lines the inside surfaces of body cavities, blood vessels and lymph vessels, making up the endothelium. The term "epithelial cell" refers to a cuboidal-shaped, nucleated cell which is generally located on the surface of a tissue. A layer of epithelial cells generally functions to provide a protective lining and/or surface that may also be involved in transport processes. The term "keratinocyte" refers to skin cells having the capability to produce keratin, including for example, cells known as basal cells, prickle cells, spinous cells, and granular cells. A hepatocyte is a cell that constitutes the main functional cells of the liver, and can constitute 60% to 80% of the mass of a liver tissue. Hepatocytes perform critical metabolic, endocrine, and secretory functions, which includes the synthesis of carbohydrates, cholesterol and bile salts, to name a few. Stem cells refer to cells having self-replicating ability and also the ability to differentiate into at least two cells, and can be divided into totipotent stem cells, pluripotent stem cells and multipotent stem cells. Myocyte refers to a differentiated, post-mitotic, muscle cell that has not undergone fusion and represents a transient cell type under most conditions. Cell from joint ligament can comprise a chondrocyte or a fibroblast from the articular ligament, peritoneal ligament or fetal remnant ligament, which are important as ligaments connect a bone to another bone to form a joint which is required for mobility. Cells from the nucleus pulposis have chondrocyte-like features. In an adult human, the cells of the nucleus pulposis obtain nutrients and eliminate waste by diffusion through blood vessels in the endplates of the vertebrate adjacent to the intervertebral discs. A HEK 293 cell is a human embryonic kidney cell line, and PER.C6® cell is a human retina cell line.

Any type of living cells may be added to the patterned substrate for culturing, including cells of the muscular and skeletal systems, such as chondrocytes, fibroblasts, muscle cells, and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue may also be used, which may provide a number of different cell types in the same structure.

In various embodiments, the living cells are selected from the group consisting of organ cells, muscle cells, nerve cells, stem cells, epithelial cells, connective tissue cells, cancerous cells (cell lines), and combinations thereof. In some embodiments, the living cells are selected from the group consisting of human embryonic stem cells (hECs), human mesenchymal stem cells (hMSCs), keratinocytes, tenocytes, ligament cells, cardiomyocytes, osteoblasts, fibroblasts, myoblasts, endothelial cells, and combinations thereof.

In specific embodiments, the one or more species of living cells is selected from the group consisting of cardiomyocytes, induced progenitor cells, smooth muscle cells, fibroblasts, and mesenchymal stem cells.

The method of the second aspect includes incubating the patterned substrate comprising the one or more species of living cells under conditions which allow proliferation of the one or more species of living cells.

Culturing the one or more species of living cells under conditions which allow proliferation of the one or more species of living cells may include incubating the patterned substrate containing the cells in the presence of a culture medium. Generally, any culture medium that allows cells to grow and/or proliferate may be used. In various embodiments, the culture medium is a nutrient-containing culture medium. For example, the culture medium may comprise or consist of an aqueous medium for culturing cells, such as one of the well known cell culture media ("growth media") available in the art, e.g. LB medium; a monosaccharide containing liquid—possibly including e.g. Hank's Salts; Eagle's minimal essential medium (including e.g. Dulbecco's Modified Eagle Medium (DMEM)); RPMI (Roswell Park Memorial Institute) medium; HyClone medium; Ham's tissue culture medium; Chee's medium; YM Broth; or Murashige and Skoog medium, to name a few, or blood.

Various cell types may attach, proliferate, and align with the aligned fibers. As mentioned above, the cells may grow along the general direction defined by the patterns present on the patterned substrate to form cells or tissues that are at least substantially aligned with the patterned surface of the patterned substrate.

The patterned substrate may be coated with chemical ligands and extracellular matrix proteins (ECM) such as, but not limited to, gelatin, fibronectin, laminin, collagen I/IV, Poly-L-Lysine, Poly-D-Lysine, or mixtures thereof to modulate cell attachment, proliferation and function.

The cells may be allowed to grow or to proliferate for a time period, in which the cells may grow to form colonies. Generally, the time for proliferation may range from a few hours or days to a few weeks, such as about 1 day to about 4 weeks, or about 1 day to about 2 weeks, or about 1 day to about 1 week. Accordingly, as time is taken for culturing cells, the implant thus formed is suitable for implantation after patient cell seeding and proliferation of the cells on the patterned substrate, while the patterned substrate is available off the shelf for such cell culturing.

The time for proliferation may also depend on the cultivation conditions for the cells. Parameters of the cultivation condition may include, for example, temperature, pH, amount of water, pressure, nutrients present, and type of cell. For example, it is well known that eukaryotic mammalian cells grow much slower in general than for example prokaryotic bacterial cells. Cultivation conditions of cells are known in the art and can therefore be adapted by a person skilled in the art depending on the desired cell type and application.

The method of the second aspect includes degrading the patterned substrate to obtain the implant. The patterned substrate may degrade naturally, wherein the term "degrade naturally" refers to subjecting the patterned substrate in an environment of intended use such that the patterned substrate is degraded. The patterned substrate may also be degraded artificially, such as by heat, chemical means, or by subjecting the patterned substrate to electromagnetic radiation. The degradation rate of the patterned substrate may be adjusted so as to suit the rate of cell proliferation. For example, the patterned substrate may be degraded at a faster rate compared to the rate of cell proliferation, so that the cells have sufficient space for growth.

An implant disclosed herein may also be used in transplantation as a matrix, for example, dissociated cells such as chondrocytes or hepatocytes to create a three-dimensional tissue or organ. Any type of cell can be added to the implant for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue may also be used, which may provide a number of different cell types in the same structure. The implant may also be used as a three dimensional in vitro culture system for attachment-dependent cells, e.g., hepatocytes in a three dimensional microenvironment which mimics the physiological microenvironment more closely.

Generally, different living cell species may be cultivated by a method disclosed herein. As mentioned above, the different living cell species may be cells from different differentiation lineages and phenotypes. The cell species may group together to form tissues. The term "tissue" refers to a structure formed by related cells joined together, wherein the cells work together to accomplish specific functions. Different types of tissues may also be arranged together to form organs. An organ refers to a differentiated structure of an organism composed of various cells or tissues and adapted for a specific function. Therefore, one or more species of living cells may be added and cultivated to form a specific organ or part thereof.

For example, the heart which is an organ contains muscle tissue that contracts to pump blood, fibrous tissue that makes up the heart valves and special cells that maintain the rate and rhythm of heartbeats. The cells may bind to and elongate along the features, and adopt a more myocyte like phenotype. Further, the cells may align and have an orientated contraction pattern, as to eventually coordinate beating contraction of the final construct. As another example, one or more species of living cells can be added and cultivated to form a skin specimen for transplantation purposes.

The aligned cells formed using methods disclosed herein may be used for various tissue engineering applications, such as growing sheets of vascular smooth muscle cells, and remodelling and maturation of isolated cardiomyocytes.

One example is human mesenchymal stem cells, which have been shown to differentiate into neuronal lineage after being cultured on nano-gratings with growth factors, or undergo osteogenic, adipogenic, and chondrogenic differentiation on aligned collagen. Another potential application area relates to human embryonic stem cells, as they may be directly differentiated to form selective neurons on nanoscale groove patterns without using growth factors. Yet another potential application area relates to the heart, whereby the heart in vivo is an anisotropic organ and the cardiomyocytes are aligned in the heart because of the arrangement of the collagen fibers. By replicating this anisotropic structure in vitro, aligned contraction, which is essential for heart function, may be produced.

In various embodiments, the implant for tissue engineering forms at least part of a vascular prosthesis or a heart patch.

Herein after, various embodiments will be described more fully with reference to the accompanying drawings, in which exemplary embodiments are shown. Various embodiments may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. Like numbers refer to like elements throughout. As used herein, the term "and/or" includes any and all combinations of one or more of the associated listed items.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the inventions embodied therein and herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1: Attributes of Scaffolds for Vascular Prosthesis

The grafts may be biocompatible in several aspects, such as non-thrombogenic, non-inflammatory, non-immunogenic, to name the three most important requirements. Generally, grafts should be compliant and elastic, and closely mimic the unique viscoelastic nature of an artery. This is especially important in applications concerning small diameter arteries. Grafts should also accommodate pressure changes, and be non-disruptive to blood flow. Furthermore, grafts should also be able to "remodel" efficiently, for example, to allow for growth of a layer of endothelium in a reasonable period of time.

Other desirable attributes of grafts include ability to be sutured or otherwise anchored in place, and ease of manufacture. Further, if the item is fabricated as an off-the-shelf item, it should be readily available for use in emergency situations. It may also be easily sterilized and available in various diameters.

A prosthesis disclosed herein may comprise a hollow tube portion and an aligned set of fibers arranged on the tube portion.

In various embodiments, the hollow tube portion is prepared by dip coating. The hollow tube portion or construct may comprise one or more biostable and/or biodegradable elastomers, such as polyurethane, and poly caprolactone-colactide copolymers, whereby ratio of caprolactone to L-lactide may range from 50% to 70%.

An aligned set of fibers made from one or more biostable and/or biodegradable polymers, preferably biostable, may be arranged on the hollow tube portion. The one or more polymers may be "spun around" the tube. The fibers are made preferably from polyurethanes and/or elastin.

The aligned fibers may also be used to orientate externally seeded cells such as smooth muscle cells or fibroblasts.

Method of fabricating the hollow tube may include surface treating a lumen surface to increase endothelial cell recruitment and retention. In various embodiments, inside of the tubular construct is treated with an alkali solution such as sodium hydroxide (NaOH). This may optionally be followed by attachment of gelatin and/or collagen either by adsorption or by chemical linkages using carbodiimides, for example.

Example 2: Fabrication of Tubular Construct Portion of Prosthesis

A tubular construct disclosed herein may be made of a synthetic material, such as PLC (poly caprolactone-lactide copolymer, in ratios ranging from 50% to 80% lactide) or other biodegradable elastomers, such as triblock copolymers of poly L-lactide and polycaprolactone (end blocks made of poly L-lactide; mid block made of a random copolymer of caprolactone and L-lactide); or star-branched copolymers of L-lactide and caprolactone; or degradable polyurethanes.

Inside of the tubular construct may be treated with sodium hydroxide only to increase surface wettability. It may be additionally treated with gelatin and/or collagen to enhance attachment of endothelial cells. The collagen and/or gelatin may be absorbed or surface immobilized through carbodiimide crosslinking, for example. The above-mentioned modifications may be optimized to promote endothelial cell recruitment proliferation and surface coverage (FIG. 1).

In various embodiments, the tubular construct may be fabricated by dip-coating. In the experiments carried out, a mandrel having a diameter suitable to create the desired lumen caliber was dip coated in a PVA solution (12% v/v) and allowed to dry for 48 hours. The PVA coated mandrel was then dipped in a solution comprising a polymer dissolved in an organic solvent. An example of organic solvent used was chloroform.

Figure 2:
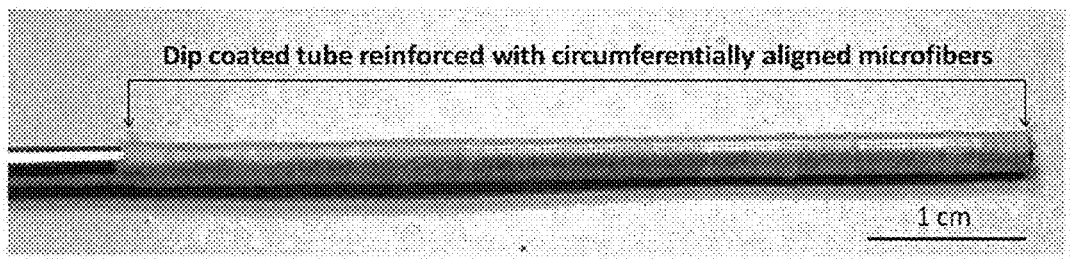
FIG. 2 is a photograph showing a dip-coated tubing on mandrel, with outer melt spun aligned fibers. The dip-coated tube is reinforced with circumferentially aligned microfibers. Scale bar in the figure represents 1 cm.
Figure 3:
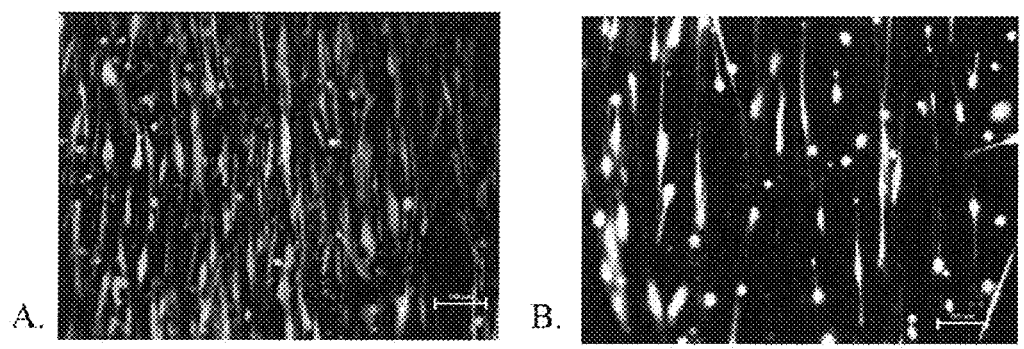
FIG. 3 shows (A) smooth muscle cells; and (B) fibroblasts, which are orientated by PCL melt spun aligned fibers. Scale bar in the figures denotes a length of 100 µm.

After two days of further drying, the tube was immersed in water so as to dissolve the PVA. This allowed easy removal of the tubular construct from the mandrel. Conduits of 10 cm to 15 cm may be fabricated in this manner (FIG. 2).

Example 3: Fabrication of Aligned Fibers of Prosthesis

The second member of the prosthesis is a wrap-around set of aligned fibers made from biodegradable polymers such as PCL or PLGA. The aligned fibers were produced by a melt spinning method. The polymer was melted, and spun at an optimized flow rate and fall height to generate a controllable fiber diameter. A melt spinneret, with x axis movement, allowed fiber collection over a predetermined span across the mandrel. Once the polymer has been spun on the mandrel with an approximate depth of two fibers, the aligned fibers were dip-coated in a binding agent to maintain their alignment.

Binding agents included chitosan (4% w/v) or gelatin (2% w/v) in acetic acid. Alignment allows for seeding of smooth muscle cells or fibroblasts in a preferred direction (circumferential) similar to the native construct.

The cells may preferably be autologous. Autologous endothelial cells may be readily obtained in useful amounts from simple procedures such dermal biopsy, regardless of patient's age. Co-seeding with stem cells was also envisaged. Stem cells have been reported to differentiate into a number of vascular cell types, such as endothelial cells and smooth muscle cells.

In the clinical setting, ex vivo seeding and stem cell differentiation were possibilities in the time frame between cell harvesting and graft application in cases of non-emergency procedures.

Generally, the cells are autologous endothelial cells. The construct may be seeded ex vivo prior to implantation. Currently, seeded vascular prosthesis used in clinics are mostly based on Dacron or PTFE materials. Selection of materials and construction according to a method disclosed herein allows fabrication of a prosthesis that mimics mechanical attributes of native blood vessels better, and which can provide better stability of endothelial cells attachment, hence very little clotting may occur after implantation.

Example 4: Endothelialization of a Dip Coated PCL Tube, to Generate a Vascular Like Conduit for Possible Graft Application and Supplying Bioreactor Construct for Vascular Like Delivery

Example 4.1: Viability of the HUVECs on the Modified PCL Films

Figure 4:
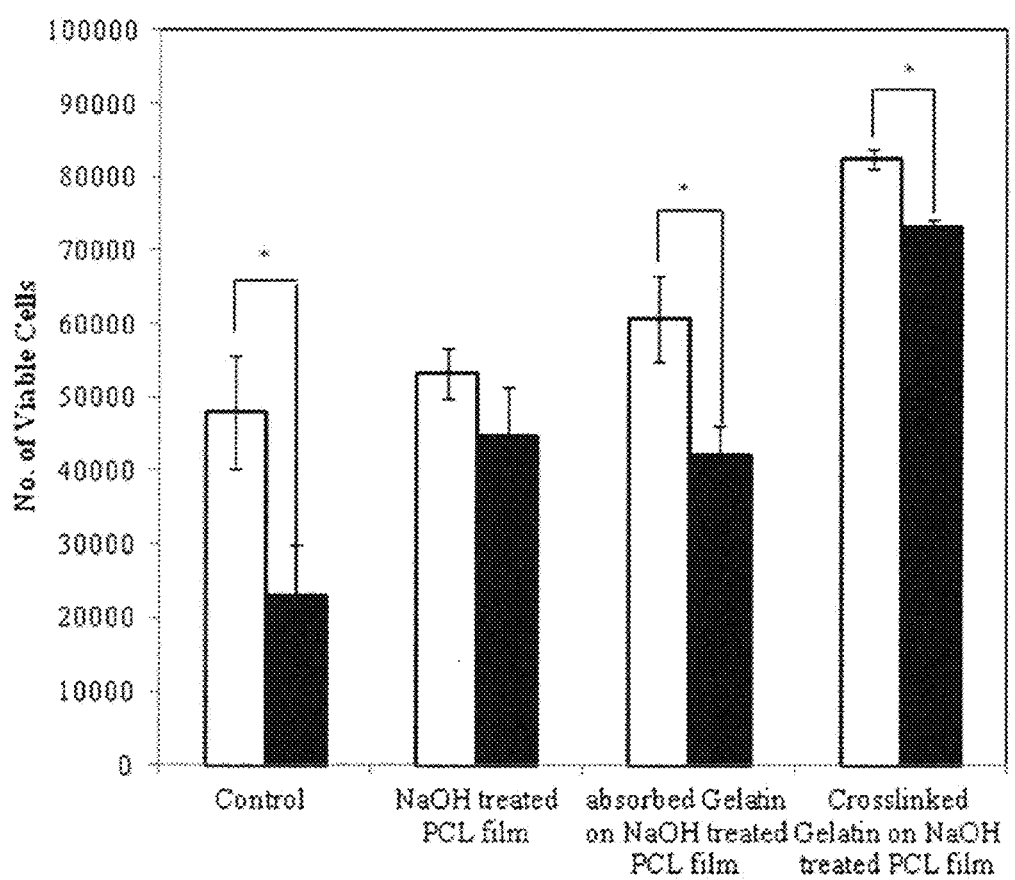
FIG. 4A is a graph showing results of a centrifugal dislodgement assay for (i) control; (ii) NaOH treated PCL film; (iii) absorbed gelatin on NaOH treated PCL film; and (iv) crosslinked gelatin on NaOH treated PCL film. Y-axis denotes number of viable cells in the range of 0 to 100000.
FIG. 4B is a table summarizing number of cells before and after centrifuge, and % cell loss.

Surface treatment of PCL with NaOH, and absorbance of gelatin and carbodiimide crosslinking for substantially increased coverage in endothelialization has been demonstrated as mentioned above. Strength of the attachment was initially tested by a centrifugal dislodgement assay as shown in FIG. 4A and FIG. 4B.

Demonstrating the gelatin crosslinked on NaOH PCL was resistant to cellular dislodgement.

This method is straightforward and convenient. However, as it has not been previously established, the cell attachment strength was corroborated using a more conventional linear flow assay.

Figures 4, 5:
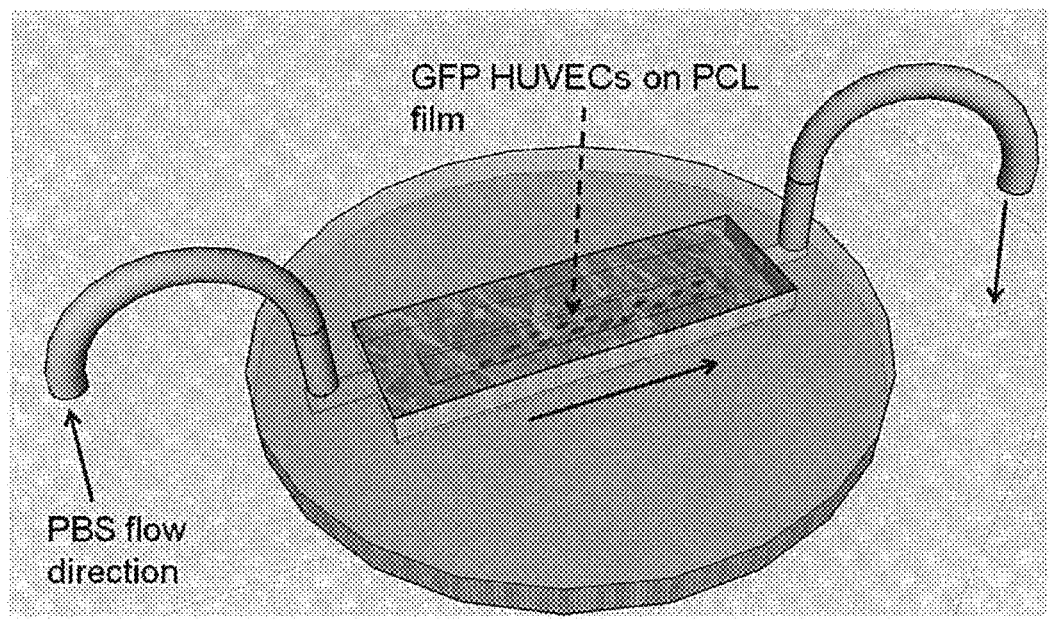
FIG. 5A is a schematic diagram showing a linear flow apparatus. The green fluorescent protein (GFP)-HUVECs were seeded on the PCL films, at a density of $10^4$ cells/cm$^2$ 24 hours prior to mounting into a parallel plate flow chamber (GlycoTech, USA), set up in-line with a phosphate-buffered saline (PBS) reservoir and a variable speed peristaltic pump (Masterflex, Cole Palmer, Ill.). The cells were presented on the PCL films within a sunken channel of 127 µm deep and a width of 2.5 mm formed by a silicon gasket placed on top of the cell-seeded films. The chamber was assembled in a 35 mm polypropylene dish, and completed with the placement of a "top deck", housing the connections to the PBS inlet and outlet tubing, enabling the flow over the adherent cells in the channel. Shear stresses (regulated by the peristaltic pump flow rate) of 15 dyne/cm$^2$ and 25 dyne/cm$^2$ were used for 30 minutes on each surface, representing the stresses within the arterial system.
FIG. 5B is a graph showing percentage retention (%) for (i) untreated, (ii) NAOH treated film; (iii) absorbed gelatin on NaOH treated film; and (iv) EDC gelatin on NAOH treated film, for shear stresses of 15 dyne/cm$^2$ and 25 dyne/cm$^2$.
Figure 5:
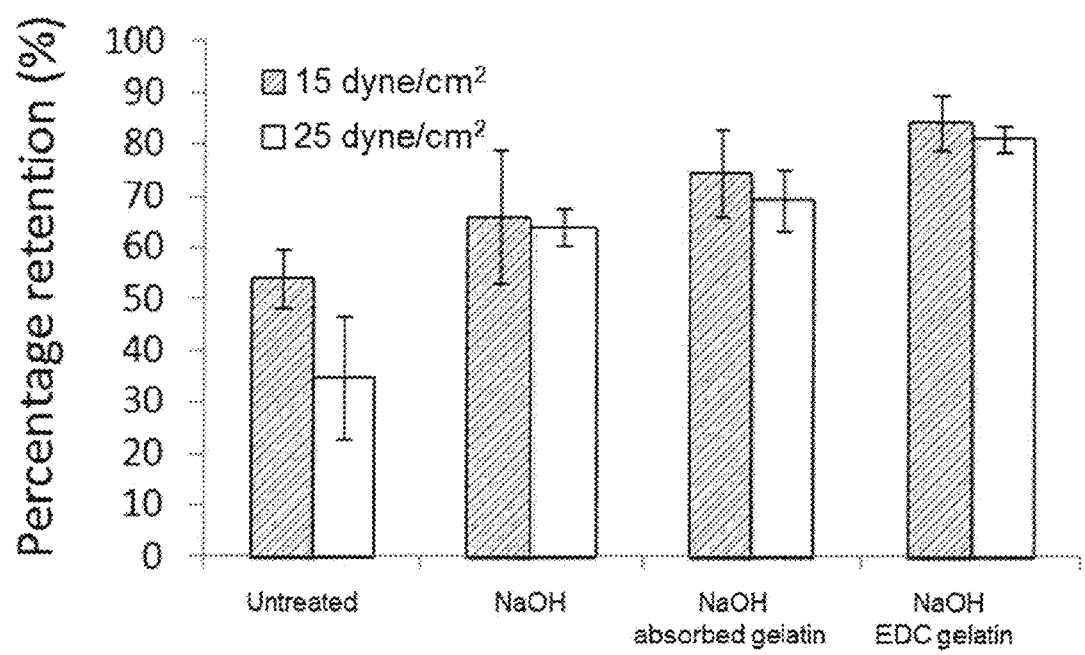

GFP expressing HUVECs on modified PCL films were placed within the linear flow apparatus (FIG. 5) and exposed to shear stresses similar to that of arterial circulation, of 15 and 25 dynes.

The cell density was monitored by counting fluorescent cells per field of view, before and after shear stress, and expressed as percentage retention after stress.

The study corroborated the centrifugal assay, in that the film modified with crosslinked gelatin retained the most cells after the application of shear stress. Hence validating the more time efficient assay and also the modification approach to promote endothelialization.

Example 4.2: Optimisation the Production and Polymer Formulation of the Vascular Prosthesis It was discovered by the inventors that an even coating of PVA on the mandrel as a water soluble layer allows effortless removal of the polymer tube. The percentage and solvent of PVA was optimized to produce even coverage for over 10 cm length of the mandrel.

Figure 6:
FIG. 6A is a photograph showing dip coating polyvinyl alcohol (PVA) using Azorubine to visualize evenness of coating.
FIG. 6B depicts an example of uneven PVA coating.
FIG. 6C depicts an example of even PVA coating (using 15% PVA dissolved in 1:1 ethanol:deionized H$_2$O).
FIG. 6D depicts PCL tube that is readily removed from dip coated mandrel using even PVA coating.
Figure 6:
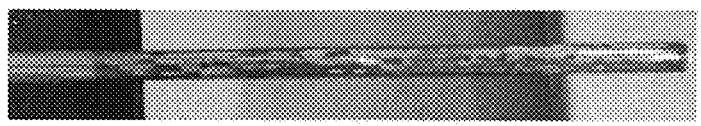
Figure 6:
Figure 6:
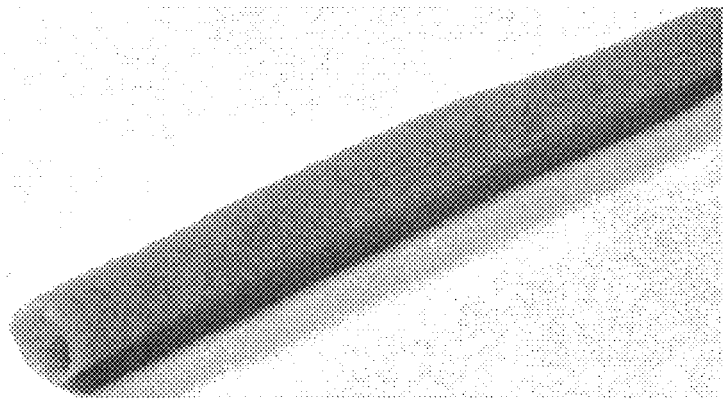

From the studies carried out, it was found that optimal blend of PVA solution consisted of 15% PVA dissolved in 1:1 solution of deionized water and ethanol, (stained with Azorubine to visualize the coating) as shown in FIG. 6.

Example 4.3: Polymer Selection Through Mechanical Studies

Different molecular weights of PCL and a similar polymer poly lactide caprolactone (PLC) of different ratios L:C were tested for their suitability to meet the requirements of a vascular prosthesis using "British International Standards ISO 7198:1998, Cardiovascular implants—Tubular vascular prostheses." as a guide.

Figure 7:
FIG. 7A is a photograph showing kick test of tube around 13 mm mandrel.
FIG. 7B is a photograph showing suture strength testing with instron.
FIG. 7C is a photograph showing burst pressure using angioplasty inflation device contain deionized water (H$_2$O).
Figure 7:
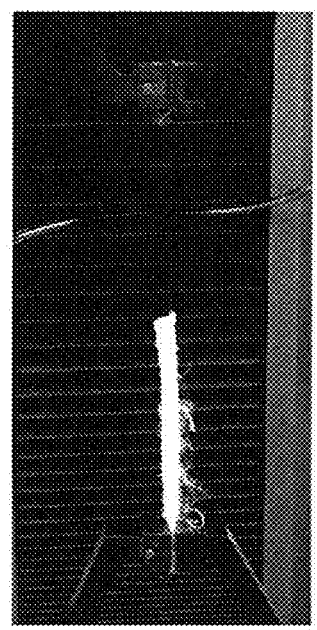
Figure 7:
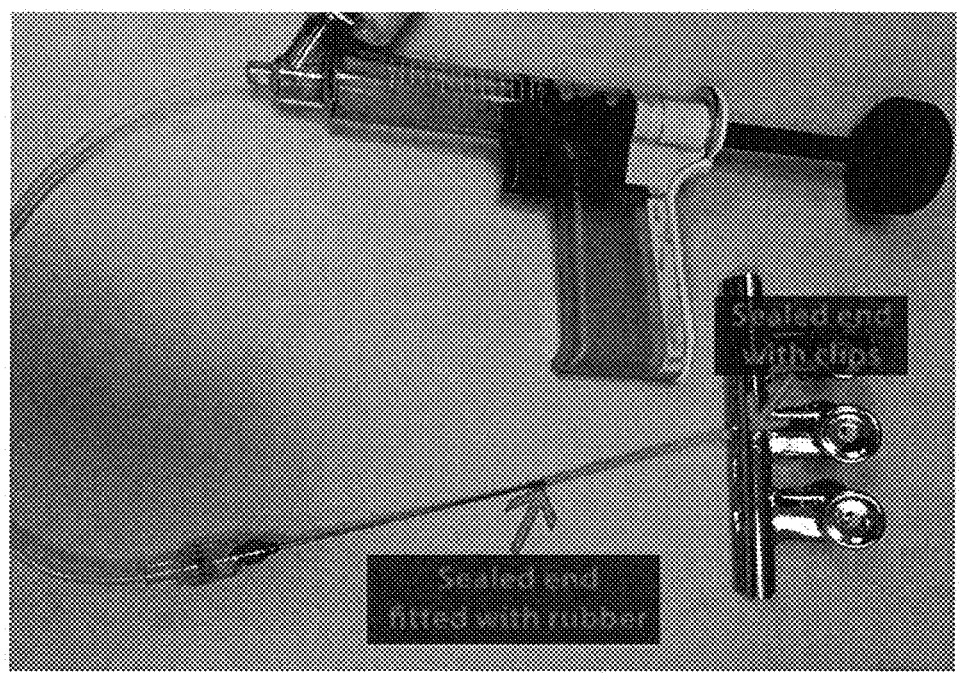

The tests carried out include; kink test, longitudinal tensile strength, suture retention strength and pressurized burst strength (FIG. 7).

TABLE 1

Quantitative results for Longitudinal Tensile Strength

| | Youngs Modulus/MPa | Ultimate Tensile Strength/MPa | Strain at break/% |
|---|---|---|---|
| PCL | 111 ± 26 | 4.8 ± 1.2 | 145 ± 110 |
| PLC 7015 | 38 ± 11 | 9.6 ± 2.2 | 291 ± 13 |
| Human Femoral Artery [1] | — | 1-2 | 63-76 |

TABLE 2

Quantitative results for Suture Retention Strength

| | Suture Strength/gf | Strain at break/% |
|---|---|---|
| PCL | 683.2 ± 215.8 | 13.9 ± 3.3 |
| PLC | Higher than 1125.1 ± 114.6 | Higher than 28.6 ± 6.9 |
| HumanTEVG (from papers) [2] | 178 ± 11 | — |
| Human saphenous vein [3, 4] | 196 ± 29 | — |
| Human internal mammary artery [3] | 138 ± 50 | — |

TABLE 3

Quantitative results for Pressurized Burst Strength

| Material | Burst Pressure/mmHg |
|---|---|
| PCL | Higher than 2250 ± 500 |
| PLC | Higher than 2250 ± 500 |
| Human TEVG (from papers) [2] | 3337 ± 343 |
| Human saphenous vein [3, 4] | 1599 ± 877 |
| Human internal mammary artery [3] | 3196 ± 1264 |

REFERENCES

[1] M. J. M. S A Sell, C P Barnes, D C Knapp, B H Walpoth, D G Simpson and G L Bowlin, "Electrospun polydioxanone-elastin blends: potential for bioresorbable vascular grafts," *Biomedical Materials*, vol. 1, pp. 72-80, 2006.

[2] A. P. K. Shannon L M Dahl, Jeffrey H Lawson, Juliana L Blum, Justin T Strader, Yuling Li, Roberto J Manson, William E Tente, Louis DiBernardo, M Taylor Hensley, Riley Carter, Tiare P Williams, Heather L Prichard, Margaret S Dey, Keith, G Begelman, Laura E Niklason, "Readily Available Tissue-Engineered Vascular Grafts," *Science Translational Medicine*, vol. 3, 2011.

[3] T. N. M. G. Konig, N. Dusserre, S. A. Garrido, C. Iyican, A. Marini, A. Fiorillo, H. Avila, W. Wystrychowski, K. Zagalski, M. Maruszewski, A. L. Jones, L. Cierpka, L. M. de la Fuente, N. L'Heureux, "Mechanical properties of completely autologous human tissue engineered blood vessels compared to human saphenous vein and mammary artery," *Biomaterials*, vol. 30, pp. 1542-1550, 2009.

[4] N. D. N. L'Heureux, G. Konig, B. Victor, P. Keire, T. N. Wight, N. A. Chronos, A. E. Kyles, C. R. Gregory, G. Hoyt, R. C. Robbins, T. N. McAllister, "Human tissue-engineered blood vessels for adult arterial revascularization," *Nat. Med.*, vol. 12, pp. 361-365, 2006.

TABLE 4

| | Sample\Diameter (mm) | | | | |
|---|---|---|---|---|---|
| | 13.0 | 12.25 | 10.15 | 9.0 | 8.35 |
| PCL (15%) | Failed | — | — | — | — |
| PCL (20%) | Passed | Failed | — | — | — |
| PLC 9517 | Passed | Passed | Passed | Passed | Passed |
| PLC 8516 | Passed | Passed | Passed | Passed | Passed |
| PLC 7015 | Passed | Passed | Passed | Passed | Passed |

Both PCL and PLC (L:C 70:30) demonstrated good longitudinal tensile strength, suture retention strength and pressurized burst strength. The values obtained met the requirements of a prosthesis. However, the kink demonstrated that the PLC was superior to the PCL. In the experiments carried out, the PCL failed the kink test on the first mandrel (13 mm) whereas PLC managed to bend round all the mandrels without kinking, down to the 8.35 mm mandrel.

Since there are some chemical and mechanical differences between the PCL and PLC, a surface modification protocol to improve cell adhesion was performed on a PLC film to demonstrate that it is still relevant to the PLC.

Figure 8:
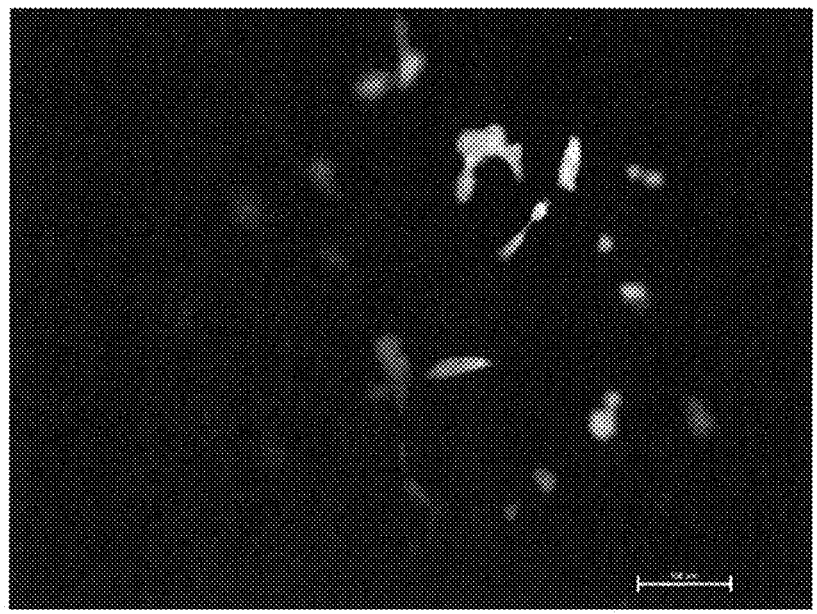
FIG. 8A shows fluorescent image of HUVECs cells on untreated poly caprolactone-lactide copolymer (PLC) films.
FIG. 8B shows fluorescent image of HUVECs cells on treated PLC films. Scale bar in the figures denote a length of 100 µm.
Figure 8:
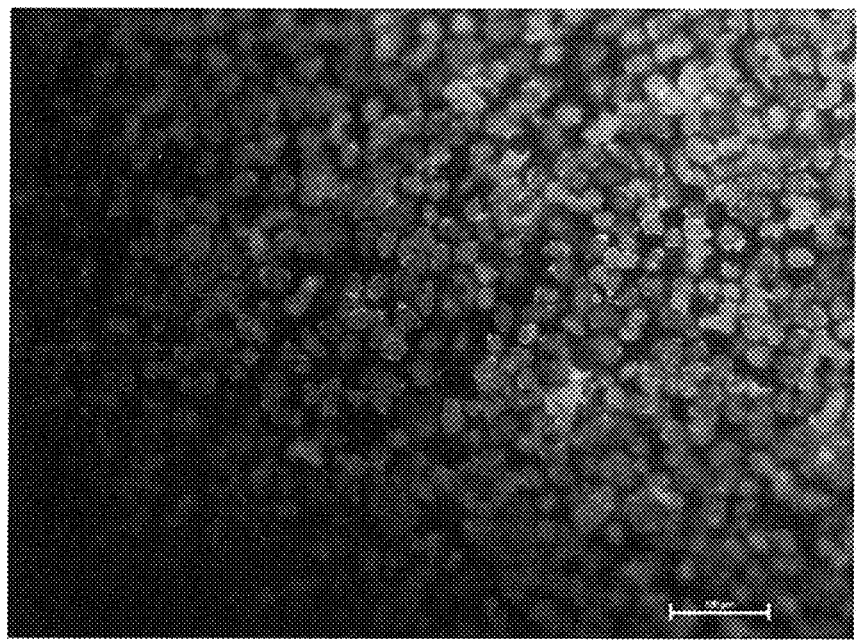

As shown in FIG. 8, the NaOH treatment and gelatin crosslinking on the PLC film surface caused a dramatic increase in the adhesion and proliferation of HUVECs creating a confluent cell layer.

Example 4.4: PLC Dip Coating Conditions

Figure 9:
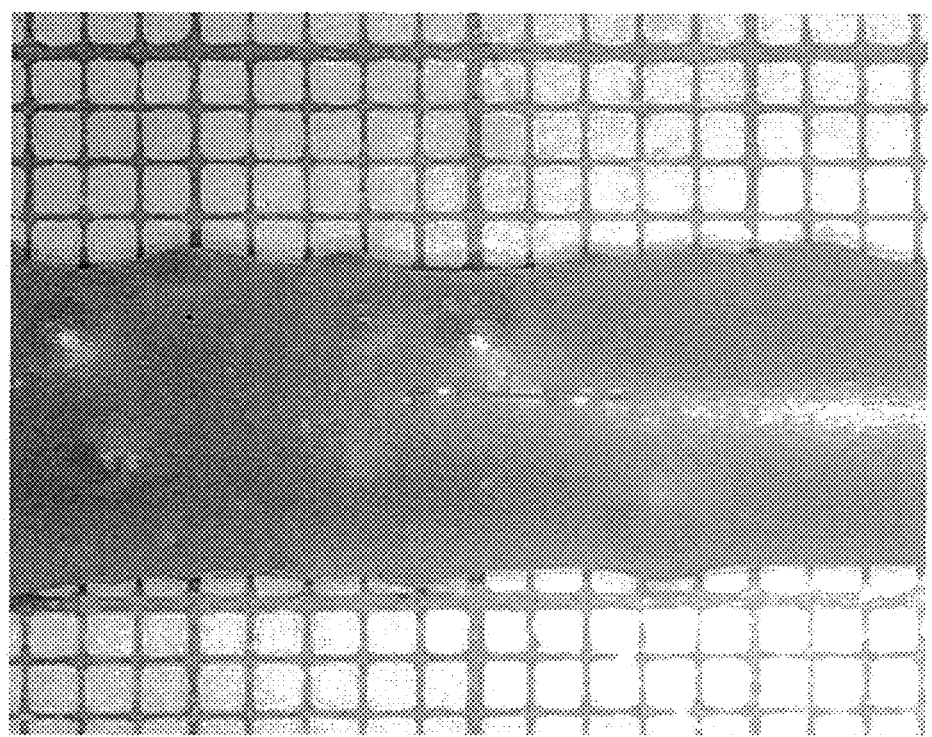
FIG. 9 depicts PLC tube for (A) uneven and unsatisfactory tube; and (B) smooth sided, even tube.
Figure 9:
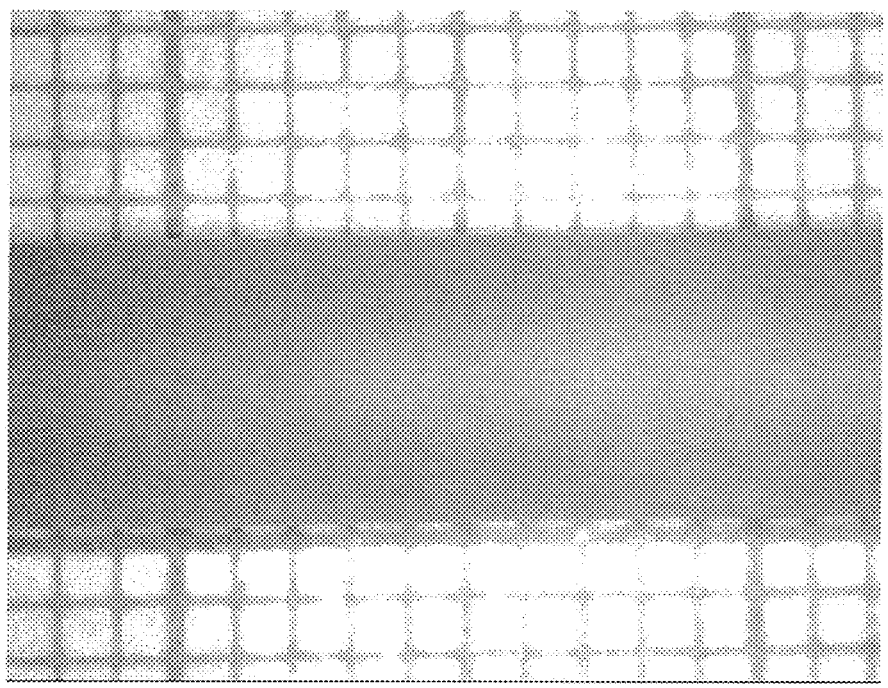

As shown in Table 5 and FIG. 9, the dip coating process was optimized to produce evenly coated tubes, which identified 15% PLC L:C ratio 70:30, fabricated with 4 dip layers produced the best tube for a prosthesis.

TABLE 5

List of different PLC grades and description of results

| Samples | L:C ratio | % wt PLC | Description |
|---|---|---|---|
| PLC-A | 70:30 | 20% 2 layers | Polymer blend too viscous, coated tubes was very uneven |
| PLC-B | 85:15 | 20% 2 layers | Polymer blend too viscous, coated tubes was very uneven |
| PLC-C | 95:5 | 20% 2 layers | Polymer blend too viscous, coated tubes was very uneven |
| PLC-D | 70:30 | 15% 4 layers | Better viscosity, more even tube, flexible and best kink resistance so far |

Example 4.5: Bioreactor Study

Figure 10:
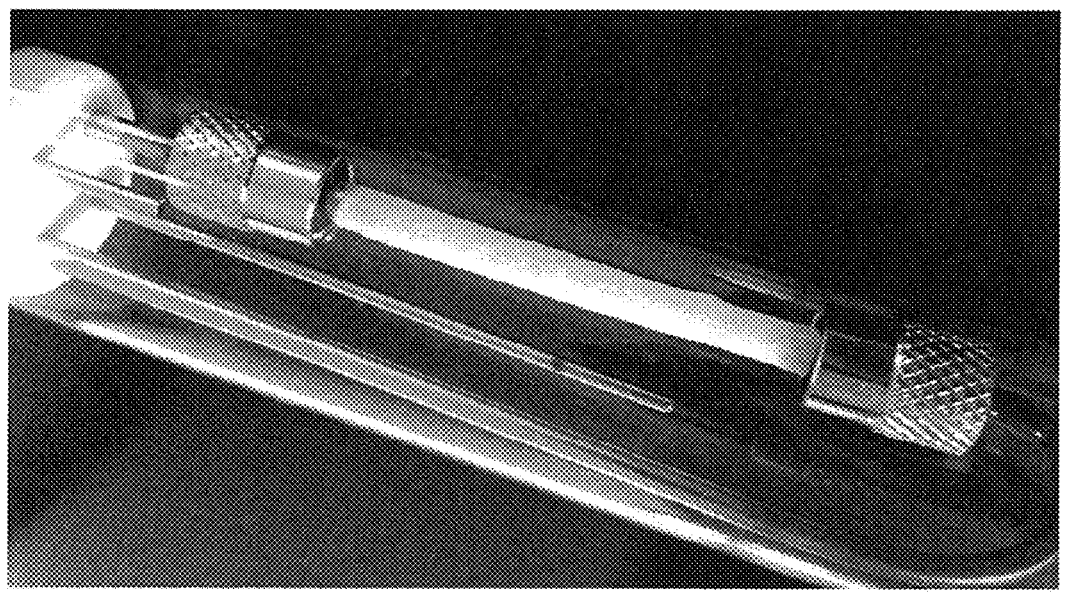
FIG. 10 shows PLC tube contained within the bioreactor apparatus for cell seeding and culturing.

As shown in FIG. 10, a bioreactor system has been set up for the seeding and culture of the prosthesis with endothelial cells in lumen and smooth muscle cells on the outside has now been established.

Example 4.6: Hydrogel Coating

An outer hydrogel coating for seeding a smooth muscle cell bearing hydrogel on the external surface of the prosthesis was carried out.

Figure 11:
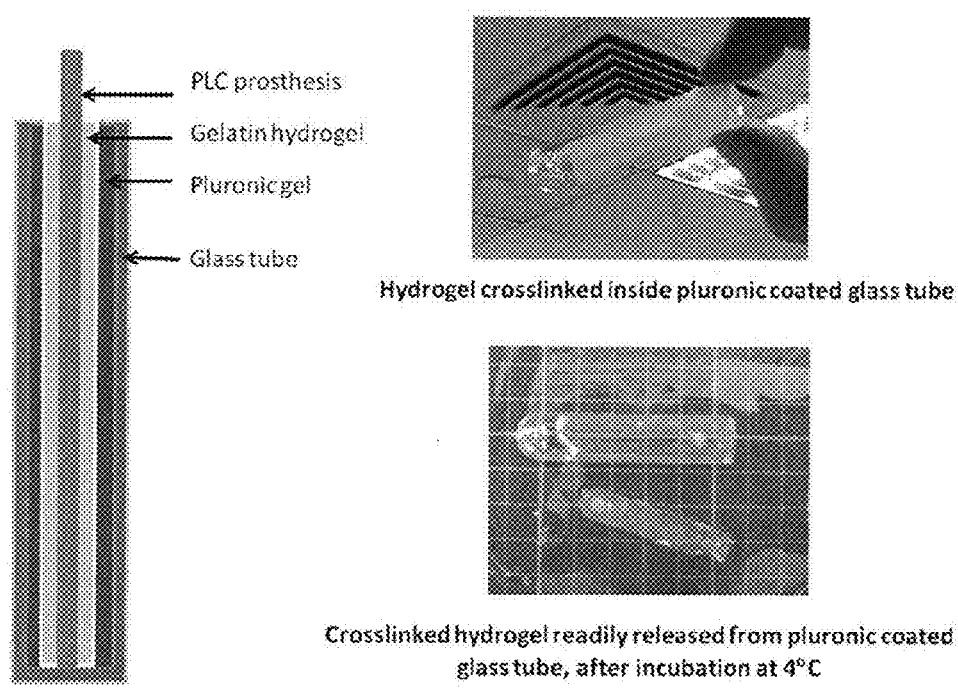
FIG. 11 shows method for coating a smooth muscle cell gelatin hydrogel on an outer surface of the PLC vascular prosthesis.
Figure 12:
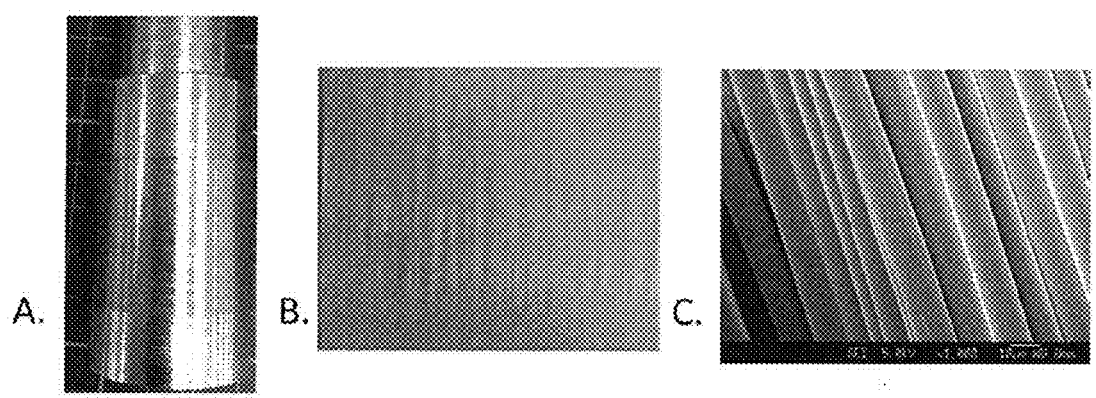
FIG. 12A shows PCL fibers spun on a stainless steel mandrel.
FIG. 12B shows an optical image of fibers (1 cm by 1 cm).
FIG. 12C shows a scanning electron microscopy (SEM) image. Scale bar in FIG. 12C denotes 10 µm.
Figure 13:
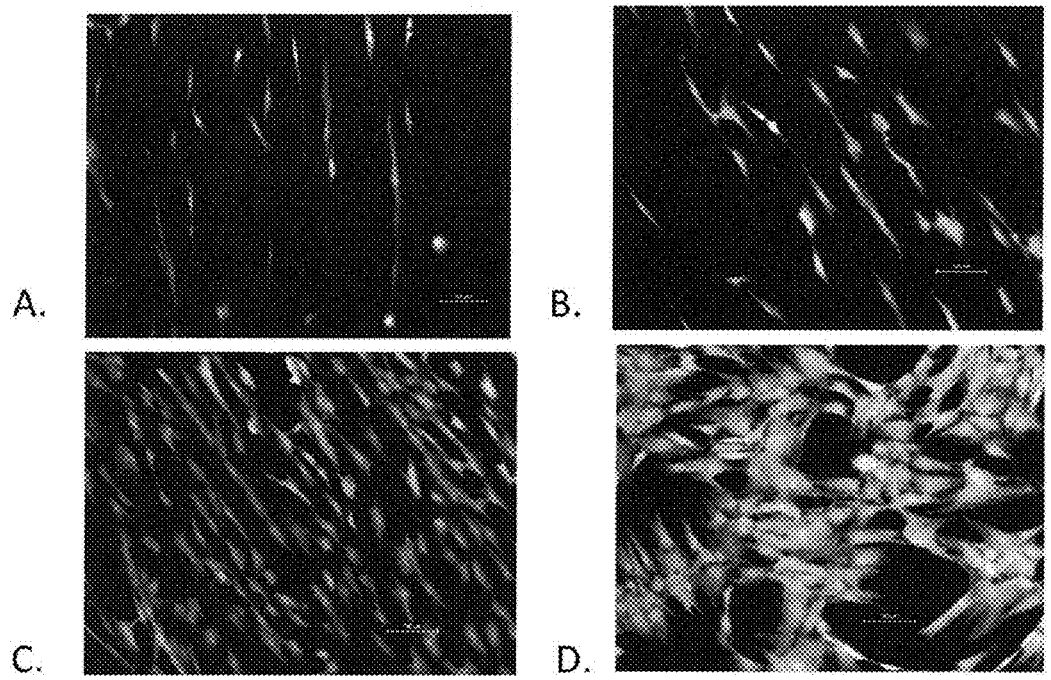
FIG. 13A shows PLC fibers coated with 4% chitosan.
FIG. 13B shows PCL fibers coated with 2% gelatin solutions.
FIG. 13C shows PCL fibers coated with 2% gelatin solutions.
FIG. 13D shows human mesenchymal stem cells (hMSCs) on tissue culture plate. hMSCs aligning in the direction of fiber orientation (All scale bars are equal=100 µm).

A gelatin gel was cast on the prosthesis in a glass tube. The glass tube was coated with pluronic gel, which underwent thermoreversible gelation at low temperatures (FIG. 11).

Example 5: Aligned Melt Spun Polymers for Cell Orientation to Promote Stem Cell Differentiation Towards Cardiomyocytes and Use as a Tissue Engineering Scaffold (a) To produce linear patterned surface, of approximately 10 μm width "channel like" feature to encourage cellular elongation in the direction of the fiber.

(b) Biocompatible material to allow the stem cells to readily attach and elongate along.

(c) Fabricated from degradable non toxic material to allow eventual disappearance of the synthetic scaffold and replacement of a natural ECM following implantation.

(d) To be easily producible, to give greater than 1 cm width and 5 cm long.

"Nice to have" Features:

(i) Sufficient elasticity to allow the material to contract with the action of beating cardiomyocytes.

(ii) To be able to separate the cells from the surface post cardiomyocyte differentiation to produce a cell sheet of aligned myocytes.

Based on these we propose a new construct designed as follows:

An aligned fibrous construct made of a synthetic material, such as PCL (polycaprolactone) or PLC (poly caprolactone-lactide copolymer, in ratios ranging from 50-80% lactide); is fabricated by melt spinning onto a turning polyethylene or stainless steel rotating mandrel, with a x axis movement of melt head to spread the deposition. The polymer sets on landing forming distinct fibers.

The deposited fibers do not adhere to each other and would not retain the aligned fiber characteristics if removed from the mandrel. Therefore a binding agent is required to keep the fibers in an aligned arrangement. PCL fibers have been bound in place by dip coating the mandrel in either chitosan or gelatin (with carbodiimide crosslinking) solution following meltspinning. PLC fibers were bound only by dip coating in chitosan solution. The dipcoated fibers were left to dry for two days before removal from the mandrel. The composition of the solution should prevent fiber shrinkage once removed from the mandrel, furthermore the materials chosen are cytocompatible, so encourage cell adhesion and proliferation.

Finally this method can also be applied to other cells that can benefit from alignment within a scaffold or an implant, such as fibroblasts and smooth muscle cells.

A process of alignment of cardiomyocytes, induced progenitor cells, smooth muscle cells, fibroblasts and mesenchymal stem cells along aligned melt spun PCL or PLC fiber held together with cross linked gelatin or chitosan is disclosed herein. Coated melt spun, aligned PCL or PLC fibers for orientating the direction of contraction for the cardiomyocytes and iPC cardiomyocyte cells are fabricated according to various embodiments.

Use of a melt spun aligned PCL or PLC fibers held together with crosslinked gelatin or chitosan as a scaffold for guiding the orientation of mesenchymal stem cells as to "aid their differentiation towards a functioning cardiomyocyte phenotype is also disclosed herein.

Fabrication of a cell seeded scaffold consisting of aligned meltspun PLC or PCL fibers held together with either cross linked gelatin or chitosan as cell guidance component within a cell seeded synthetic polymer scaffold within a bioreactor is disclosed herein.

Fabrication of a cell seeded scaffold consisting of aligned meltspun PLC or PCL fibers held together with either cross linked gelatin or chitosan as cell guidance component within a cell seeded synthetic polymer heart patch for implantation is also disclosed herein.

A process for the production of the aligned construct comprising: melt spinning PCL or PLC onto a turning polyethylene or stainless steel rotating mandrel, with a X axis movement of melt head to spread the deposition; the deposited fibers bind in place by dip coating the mandrel in either chitosan or gelatin solution; the dipcoated fibers are left to dry for two days before removal from the mandrel.

Figure 14:
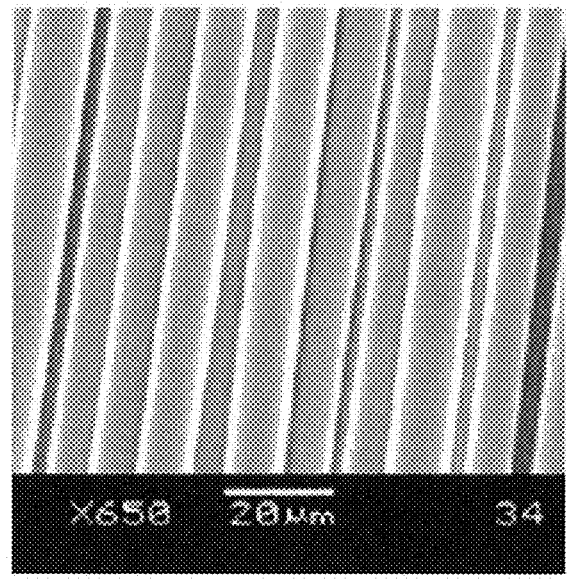
FIG. 14A shows SEM image of aligned PCL fibers generated by melt spinning.
FIG. 14B shows fibers bound in position with a chitosan glue removed from the mandrel.
FIG. 14C shows fibers without chitosan glue, demonstrating unraveling. Scale bar in (A) denotes a length of 20 µm.
Figure 14:
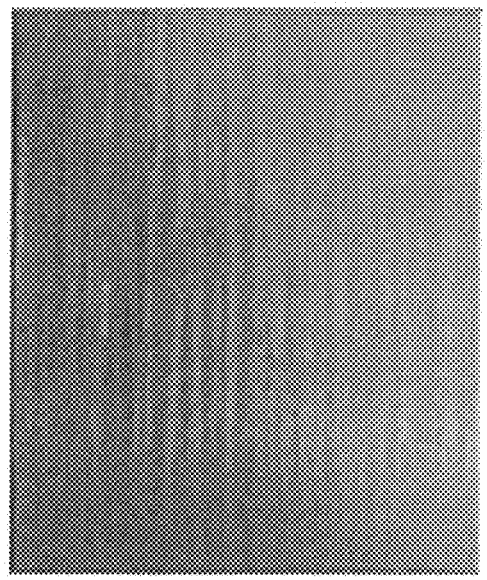
Figure 14:

Aim of this study is to create anisotropic fibrous scaffold to align seeded, smooth muscle cells, fibroblasts, Human Mesenchymal Stem Cells (hMSCs) and cardiomyocytes. Polycaprolactone (PCL) and poly(L-lactide-co-ε-caprolactone) (PLC) were chosen to melt fabricate the aligned fibers, due to their different mechanical properties such as elasticity and flexibility. Fiber scaffolds were fabricated by melt-spinning process and collected on a rotary mandrel. Collected fibers immersed in chitosan (4%) solution as binding agents, to retain their alignment during handling, and bioactive molecules, to improve cell attachment and proliferation (FIG. 14).

Figure 15:
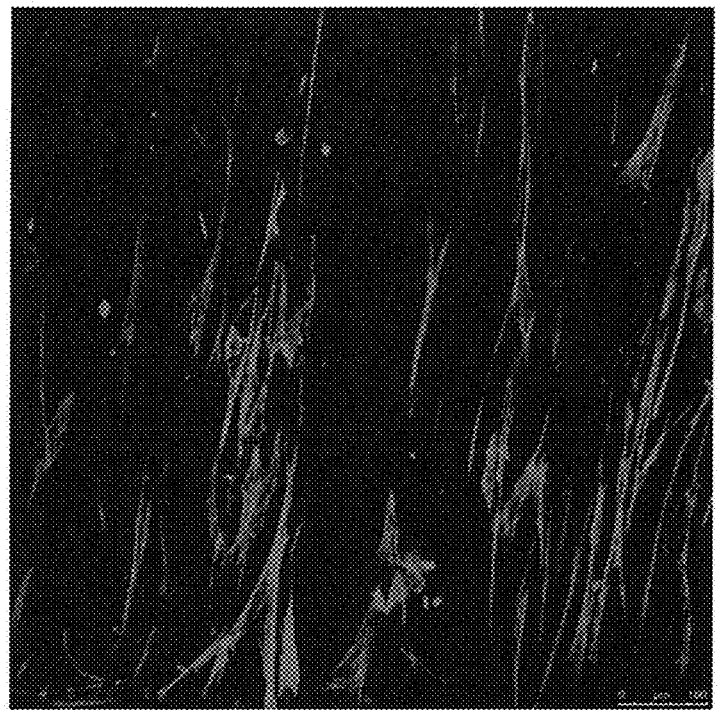
FIG. 15 shows smooth muscle cells on (A) aligned fiber; and (B) random fibers. The images are stained with F-actin. Also shown are aligned smooth muscle cells on (C) aligned fiber day 3, and (D) aligned fiber day 7; and (E) non-aligned smooth muscle cells day 3 and (F) day 7. The cells are stained for α-Smooth muscle cell actin stain, a marker for the contractile phenotype.
Figure 15:
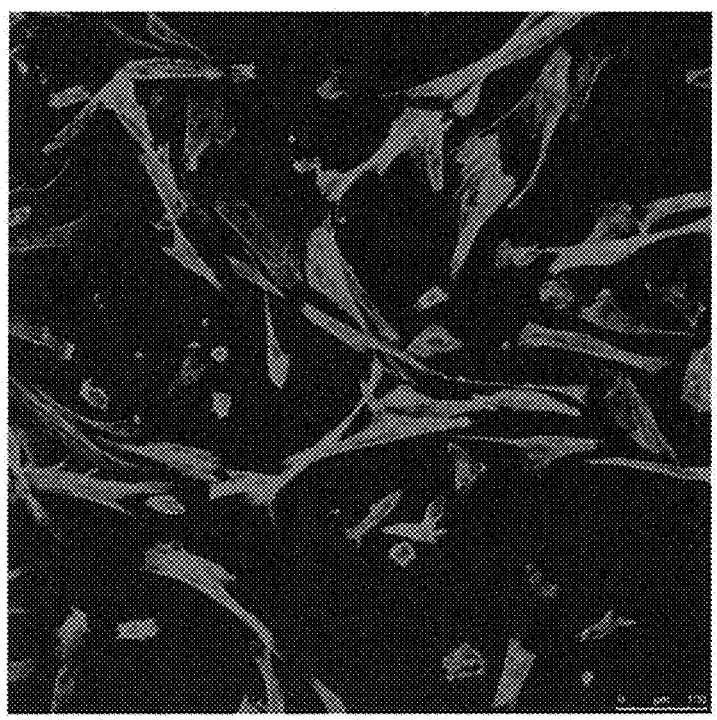
Figure 15:
Figure 15:
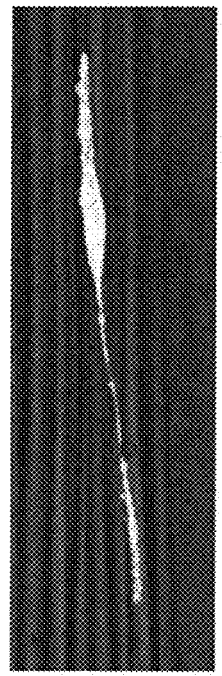
Figure 15:
Figure 15:
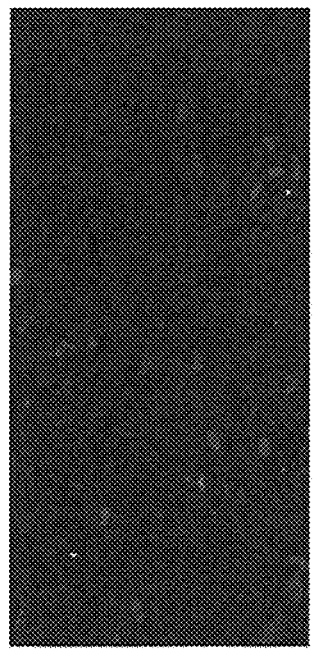
Figure 16:
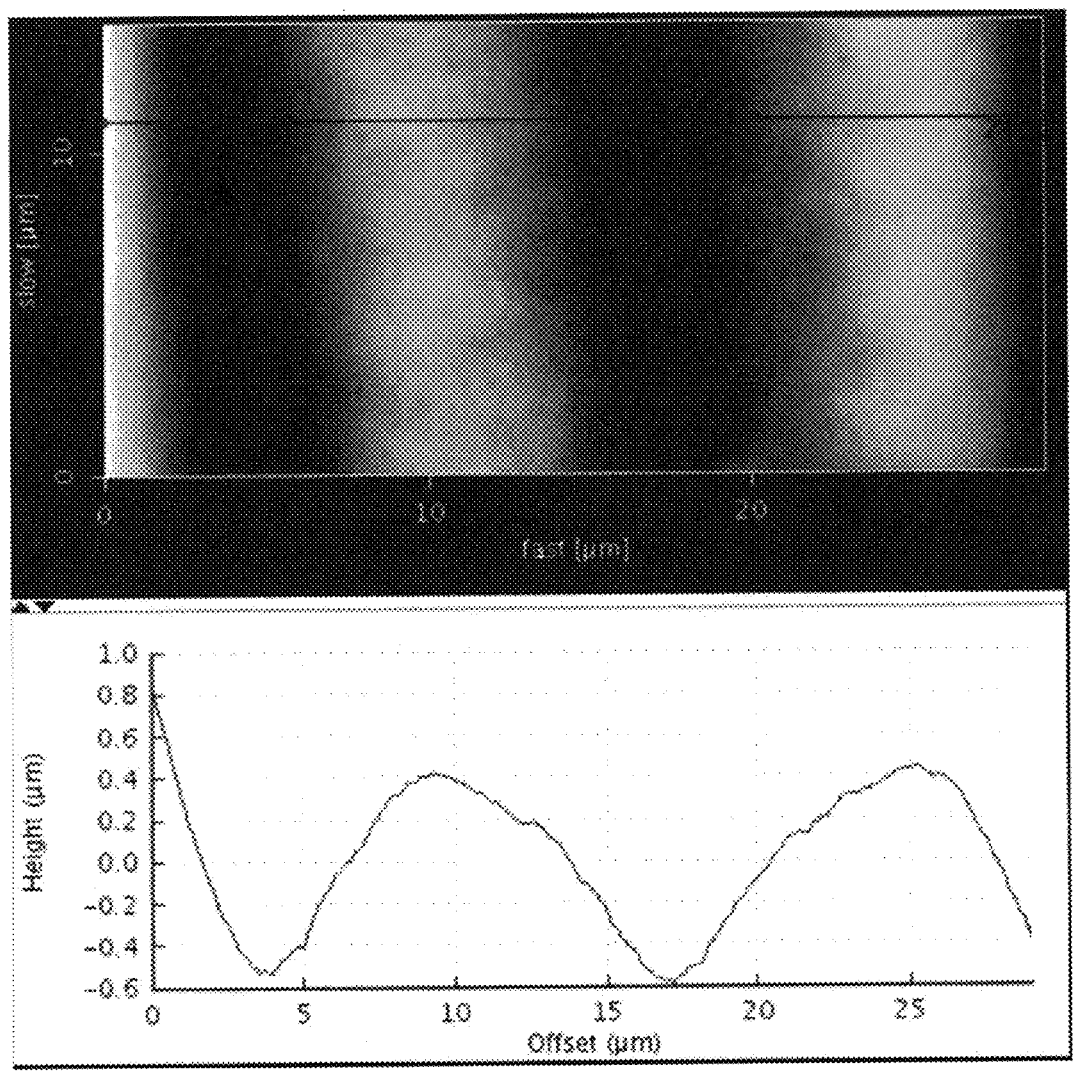
FIGS. 16(A) and (B) depict surface analysis of the aligned chitosan covered fibers, where (A) atomic force microscope (AFM) image and report of the aligned fiber surface's topographical features bonded by chitosan; and (B) Fourier transform infrared spectroscopy (FTIR) report of the aligned chitosan film and PCL coated chitosan. For (B), y-axis: % T; x-axis: cm$^{-1}$ in range from 4000 to 650.
Figure 16:
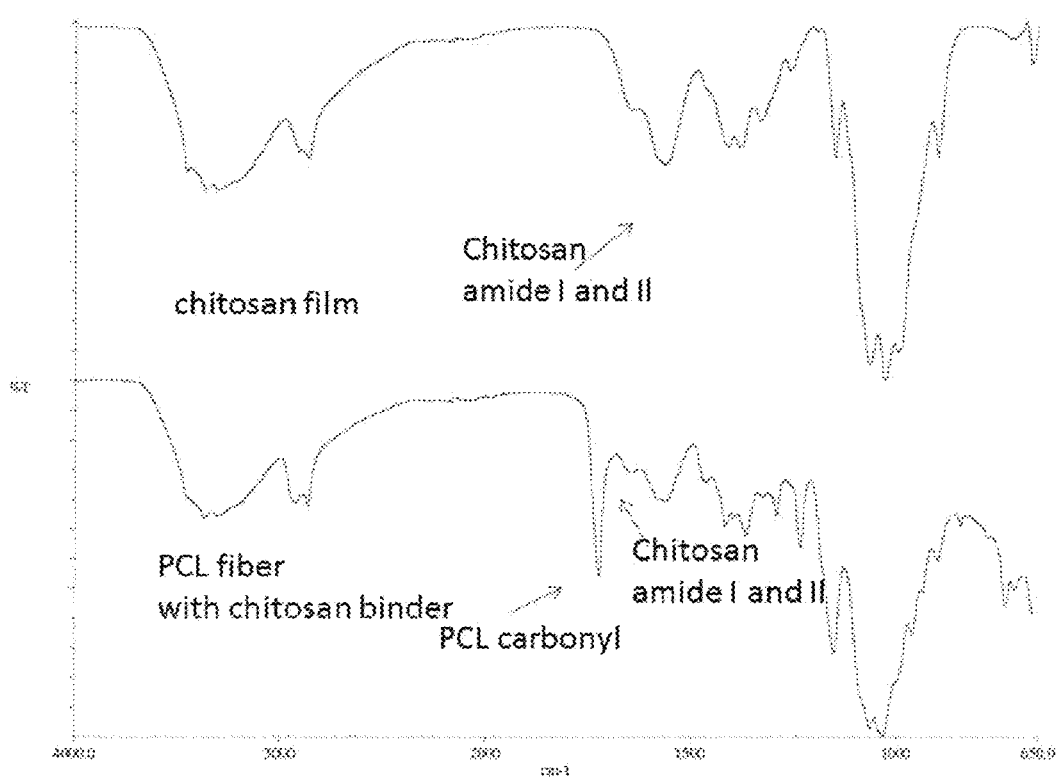

Effect of fibers on cell alignment and phenotype was assessed on other cell types. Fibroblast and smooth muscle cells (SMCs) were also found to be able to orientate on melt spun fibers. The cells were cultured on the scaffold and growth and orientation were monitored. The cells were observed to orient along the direction of the fibers, whereas cells on random fiber meshes displayed no such directional arrangement. Although differentiated, SMCs have plasticity between two distinct functional phenotypes: secretory and phenotypes. To assess the effect on smc phenotype, cells on aligned fiber were stained with α-smc actin, a marker for the contractile phenotype. The inventors have found that recently passaged cells (day 3) expressed the α-smooth muscle cell actin on aligning and non aligning surface (FIGS. 15C and 15E), however this phenotype was only maintained after 7 day on the aligned fiber surface (FIGS. 15D and 15F). This result implies that the aligned fiber surface is able to preserve the contractile phenotype, a property which will be useful for use in a vascular prosthetic. Atomic force microscopy (AFM) results demonstrate that the chitosan adhered fibers produces aligned grooves of approximately 15 μm wide with a surface coating of chitosan to promote cell adhesion (FIG. 16).

This aligned scaffold can now be incorporated into the vascular prosthesis project as an approach to align smooth muscle cells and fibroblasts. The circumferential alignment, of SMC in particular, is proposed to aid vasomotive function and compliance. Indeed, the mandrels used to dip coat the vascular prosthesis can be inserted into the melt spinning apparatus and a prototype with the PCL aligned fiber surrounding the PLC has been constructed.

Example 6: Aligned Polycaprolactone (PCL) Meltspun Fiber Scaffold for the Orientation of Vascular Fibroblasts and Smooth Muscle Cells A highly aligned melt spun PCL fiber scaffold that allows fibroblast and VSMC attachment and which also preserves the phenotype of the VSMC contractile cells has been demonstrated.

Meltspun PCL fibers were deposited on a mandrel to form aligned fibers of 10 µm in diameter. The fibers were bonded into the aligned arrangement through dip coating in chitosan solution. This formed a surface of parallel grooves, 10 µm deep by 10 µm across which presented a surface layer of chitosan to promote cell surface interactions.

The aligned fiber was used as a surface to culture cells present in the vascular wall, in particular fibroblasts and smooth muscle cells. This surface induced "surface guidance" over the orientation of the cells, which adopted an elongated, spindle like characteristic, whereas cells on the unpatterned control surface did not show such orientation and assumed a more rhomboid shape characteristic. Preservation of the VSMC contractile phenotype on the aligned scaffold was demonstrated by retention of α-SMA expression after several days of culture. The control of SMC phenotype is beneficial towards producing a tissue engineered blood vessel to harness natural functionality of cells.

Example 6.1: Materials and Methods

Melt spinning of polycaprolactone was performed by melting powdered PCL (50 kDa) at approximately 120° C., and then drawn by gravity to mandrel at 750 rpm.

Example 6.2: Fourier Transform Infrared Spectroscopy

FTIR analysis was used to qualitatively characterize functional groups introduced and/or presented on the surface of the construct. FTIR spectra were collected with Frontier FT-IR spectrometer (PerkinElmer) at resolution of 4 cm$^{-1}$ and signal average of 16 scans in each interferogram over the range of 4000 cm$^{-1}$ to 600 cm$^{-1}$. Two measurements were retrieved on two random locations per sample for each group. Results were analyzed by plotting % transmission against wavelength (nm).

Example 6.3: Atomic Force Microscopy (AFM)

Intermittent contact mode atomic force micrographs were obtained on JPK Instruments Nanowizard III (Aufgang C, Germany) with a nanoprobe of 100 µm length and a rotated monolithic silicon narrow cantilever with a force constant of 40 Nm$^{-1}$ and a tapping frequency of 300 kHz.

The tapping mode AFM conditions were as follows; 0.4 Hz scan rate, set point was 1.5 V, drive amplitude was set to 0.5 V and the drive frequency was approximately 280 kHz. Adjustments of the integral gain, proportional gain, and set point was done to minimize contact force and electronic noise as well as to maximize the features of the sample. The AFM micrographs was evaluated by flattening the images (second-order) with the help of Nanowizard Data Processing JPK Software.

Example 6.4: Cell-Seeded PCL Fiber Film

Smooth muscle cells (SMCs, Lonza) or human fibroblasts were cultured up to 8th passage in smooth muscle cell basal medium (SmGM-2 Media (Lonza Bioscience)) or FibroGRO™ Complete Media (Millipore) respectively. PCL fiber films (1×1 cm$^3$) were sterilized with 70% ethanol for 1 h and then were washed away with PBS (three times). The cells (about) were seeded on the PCL fiber films and a control surface at a density of 5×10$^4$ cells/cm$^2$. Cell-seeded fibers were cultured in a flat bottom 24-well plate for 7 days.

Example 6.5: Immunofluorescence Imaging with Confocal Microscopy

The seeded fibroblasts were recorded after 14 days. The fluorescence was generated by 30 minute incubation with 2 µM Calcein AM in PBS.

SMCs in cell-seeded fibers at day 3 and day 7 were fixed in 4% paraformaldehyde for 30 min in room temperature. Following fixation, fibers were washed 3 times with PBS, permeabilized with 0.1% Triton X-100, blocked using 2% BSA in PBS for 1 h in 4° C. After washing 3 times at room temperature, and immunohistochemical labelling on fibers and control (chitosan film) samples was performed, applying primary antibody against alpha smooth muscle actin (monoclonal mouse anti-human), at 1:100 dilutions in PBS/BSA/ buffer at room temperature for 2 h. After washing 3 times for 10 min in PBS/BSA buffer, secondary antibodies (AF 488 goat anti-mouse, Invitrogen) were applied at 1:200 dilutions in PBS/BSA buffer at room temperature for 1 h. Cell nuclei was stained with DAPI (4',6-diamidino-2-phenylindole) and PCL fibers were then imaged via confocal microscopy (Leica, Wetzlar, Germany).

Example 6.6: Results

The melt spin method produced a thin layer of highly aligned PCL fibers of 10 µm width on a mandrel within approximately 15 minutes, creating aligning fibers of 10 µm diameter (FIG. 14A). The PCL is a melt spun into nonbonded, distinct fibers that readily unravel (FIG. 14C). Hence, the chitosan dip coating allows for an adhesive effect for the fibers to be removed from the mandrel as an aligned fiber mat (FIG. 14B).

The fiber mat was examined by AFM (FIG. 16A) and FTIR (FIG. 16B). The FTIR demonstrated a strong signal for the characteristic amide groups of chitosan, hence the chitosan coats the fibers and becomes the principle substrate for cell interactions. The chitosan amide groups are known to help provide for a cytocompatible surface to the device. From the AFM, it appears the fibers form curved grooves approximately 10 µm and 10 µm deep, a depth which allow cells to make contact with other cells growing in neighbouring grooves as seen in FIGS. 17A and 17C. In addition, the chitosan gives the scaffold a roughened surface feature, unlike the relative smooth surface of pristine PCL.

Fibroblasts were seeded onto the fiber surface and readily aligned with the parallel fibers, becoming noticeably elongated compared to the control (FIGS. 17A and 17B). These cells continued to proliferate until reaching 100% cell confluency. Similarly for SMCs, it was observed that after 7 days the cells adopted a stretched morphology that followed the orientation of the fiber, resembling the spindle like appearance of the contractile cells (FIG. 17C). In comparison the SMCs seeded on chitosan film grew without obvious orientation and present a rhomboid appearance akin to the secretary phenotype (FIG. 17D). Interestingly, unlike the fibroblasts, the fiber seeded SMCs were not observed to proliferate towards confluency.

As a phenotype marker, the cells on the fibers were fixed and stained for alpha smooth muscle actin. The expression of this contractile marker gave a strong signal for both surfaces on day 3 post seeding. However, the α-SMA decreased after 7 days for the fiberless chitosan film, whereas the SMCs on the aligned fibers retained a considerable expression (FIG. 17D), hence the SMCs on aligned fiber retain a more contractile like phenotype for several days, whereas on the chitosan film it becomes more secretory like.

Example 6.7: Discussion

The method of meltspinning PCL for the aligned orientation of both cell types and the phenotype regulation of SMC disclosed herein will be of considerable use to the design of TEBV. Indeed, it has been demonstrated herein that polymer tubing (fabricated from PCL) on a mandrel can be decorated with circumferential aligned meltspun PCL.

Fibers removed from the mandrel without the chitosan bonding separated very readily. Furthermore polycaprolactone without modification has poor cell adhering properties, whereas chitosan with high deacetylation (85% to 95% in this case) has very good cell recruiting qualities. The higher the deacetylation, the greater amount of free amino groups that forms cationic amine groups which in turn encourage cell adhesion to the surface. The smooth pristine PCL also lacks the surface roughness that facilitates the cells establishment of adhesion points, whereas the chitosan coating gives a considerably more roughened surface feature. Furthermore, the AFM revealed that the chitosan covering does not fill in the space between fibers but instead leaves a distinct, curved sided groove that facilitates the aligned orientation of the cells.

Previous studies have demonstrated that freshly seeded SMC are often display a strongly contractile phenotype. Following a prolonged period of culture, the cells gradually become predominantly synthetic. In the present study, the inventors have found SMCs seeded on chitosan films also began with notable expression of α-SMA. This expression is considerably diminished after several days, indicating a move towards the secretory. The cells seeded on the aligned fibers also showed substantial expression of αSMA 24 hours post seeding, however this expression was retained after several days, indicating the preservation of the contractile state.

The cell growth of the fiber seeded SMCs was qualitatively less than the fiber seeded fibroblasts and the chitosan film seeded SMCs following 7 days of culture even though initial seeding was identical. It is widely known that a reduction in proliferativity is associated with the transdifferentiation towards the contractile phenotype. Hence, a parallel fiber scaffold will require an initial cell seeding at a high SMC concentration to generate sufficient cell coverage rather than relying on cell growth to acquire suitable SMC coverage.

The method disclosed herein has substantial advantages over electrospinning; firstly the whipping action of electrospinning limits the exact alignment. To get an aligned structure by electrospinning a narrow rotating disk collector is used for fiber collection thus generating aligning surfaces of limited width.

Figure 17:
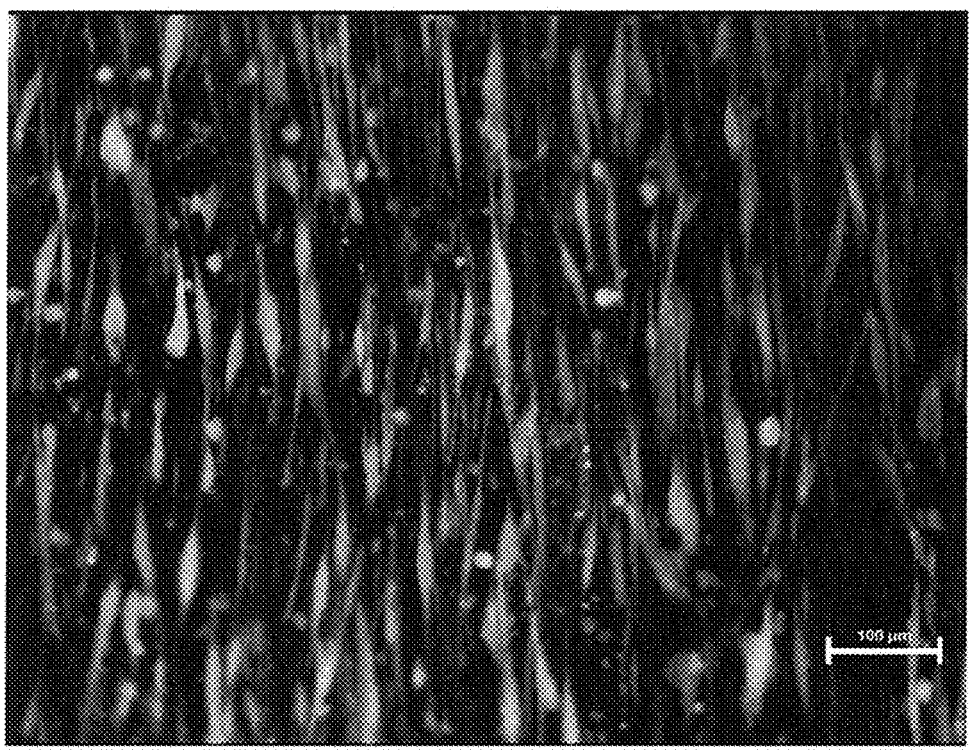
FIG. 17 shows SMCs orientated on (A) melt spun aligned fiber, and (B) cultured on chitosan film for several days. The cells are immuno stained for F-actin and 4',6-diamidino-2-phenylindole (DAPI) nuclear stain. Fibroblasts cultures on (C) aligned fiber, and on (D) tissue culture plastic, for 14 days. Scale bar in the figures denote a length of 100 µm.
Figure 17:
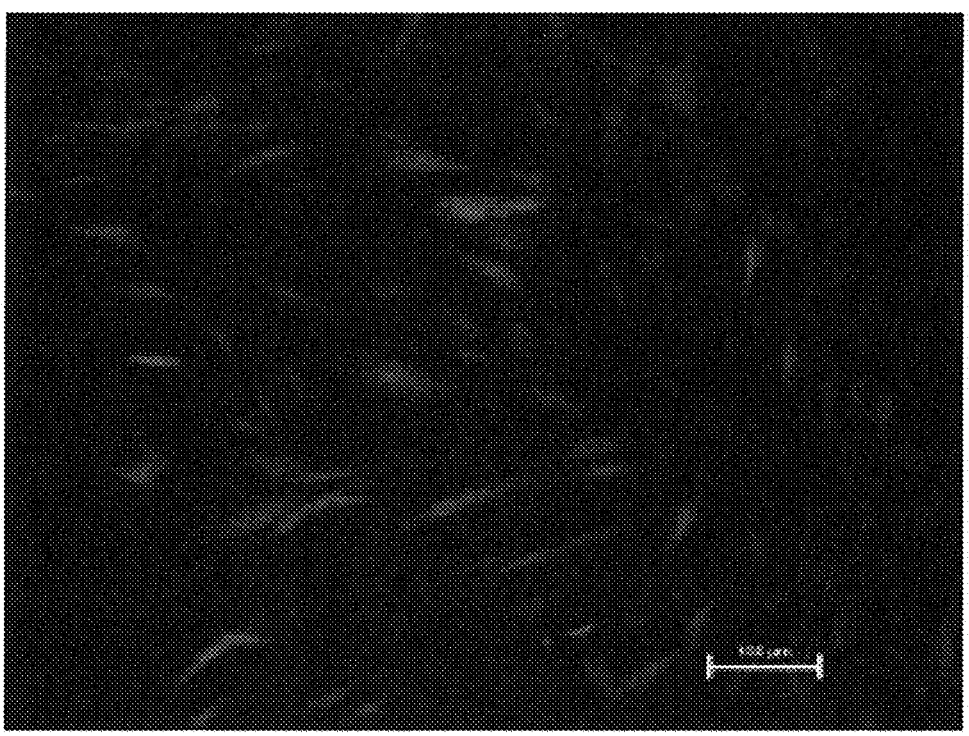
Figure 17:
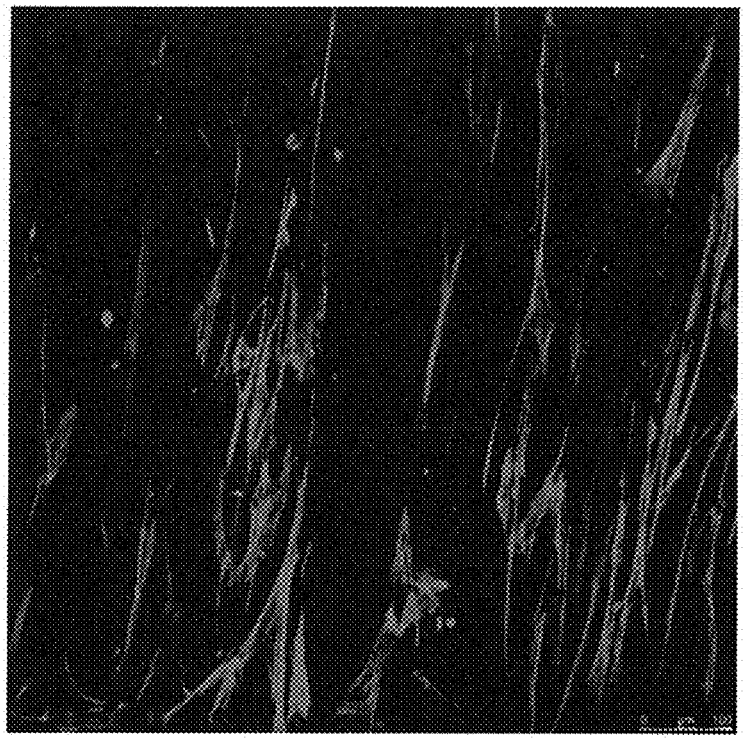
Figure 17:
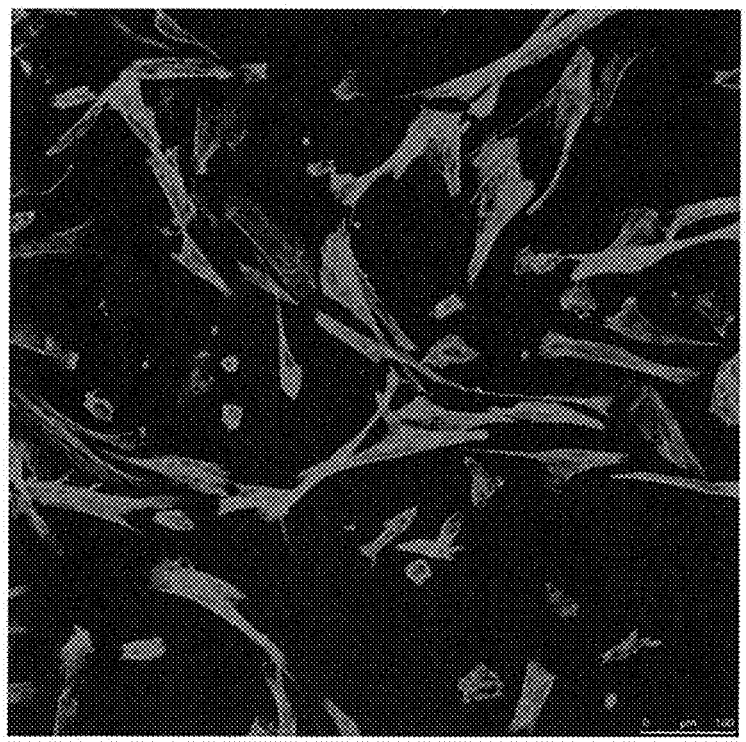
Figure 18:
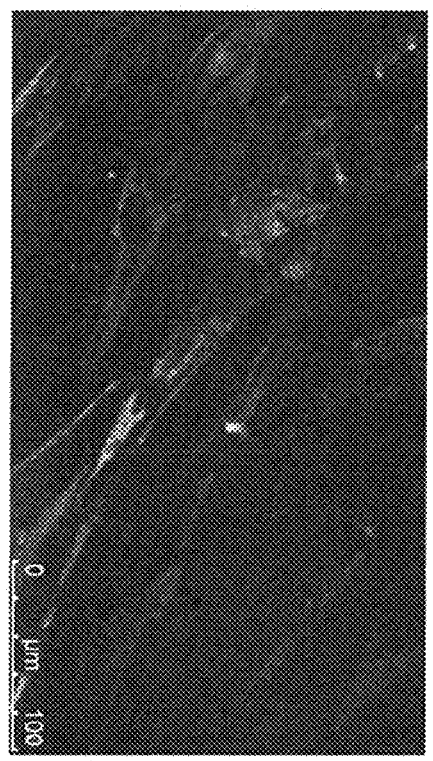
FIG. 18 shows smooth muscle cells (SMC) expression of α-SMA. (A) SMCs cultured on chitosan films for 3 days; (B) on chitosan film for 7 days; (C) SMCs on aligned chitosan coated PCL after 3 days; and (D) aligned on chitosan coated PCL after days. All cells stained for α-SMA and with DAPI nuclear stain. Scale bar in FIG. 18(A) denotes a length of 100 µm.
Figure 18:
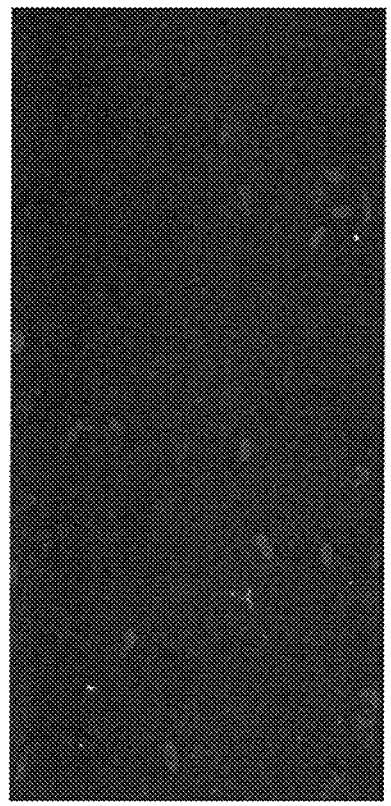
Figure 18:
Figure 18:
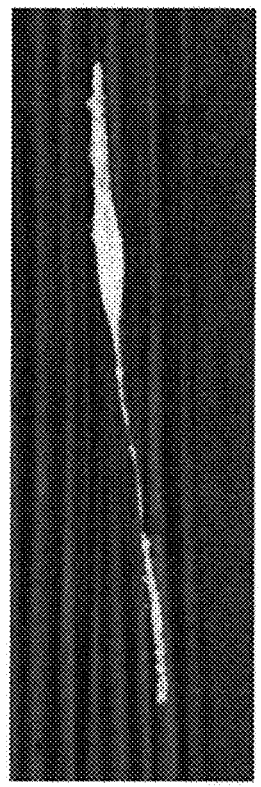

The current study employed micro diameter scaffolds. The melt spun fibers have a diameter of 10 μm, similar to the width of adhering, elongated cells. In a comparable study, on microsized fibers produced by wet spinning of PLGA, it was found that as the diameter of fibers increase, the degree of orientation decreases from 10 μm to 242 μm. The larger diameter fibers having cellular alignment similar to planar surfaces. Hence, the fibers created by meltspinning disclosed herein are in favorable width range for promoting cell alignment. In addition, their relatively low groove depth allows fibroblast and SMCs to grow closely together as seen in FIG. 17, unlike other methods that produce much deeper channels or wider intervals.

This ability of fabricating and controlling alignment patterns on tissue engineered devices will aid the production of a more physiological like representation of natural tissue. Moreover, since the melt spun technique is delivered to a mandrel, it can be adapted to introduce circumferential aligned pattern on the outer surface of a synthetic polymer TEBV, if positioned in the place of the rotating mandrel. Thus allowing the alignment of cells that comprise the outer vasculature layers, i.e. fibroblasts and SMCs.

Figure 19:
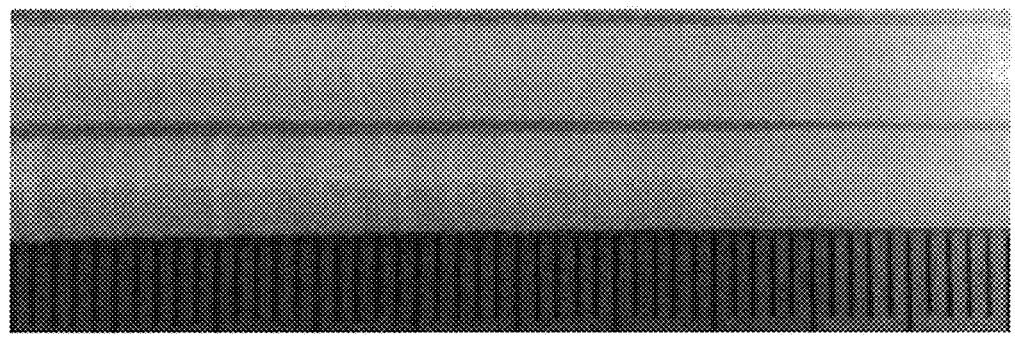
FIG. 19 shows aligned melt spun fibers deposited circumferentially onto a small diameter (4 mm) PLC conduit. The PCL melt spun fibers are able to pattern the outer surface of a 15 cm long PLC prosthesis, for supporting the seeding with VSMC (see FIG. 20).
Figure 20:
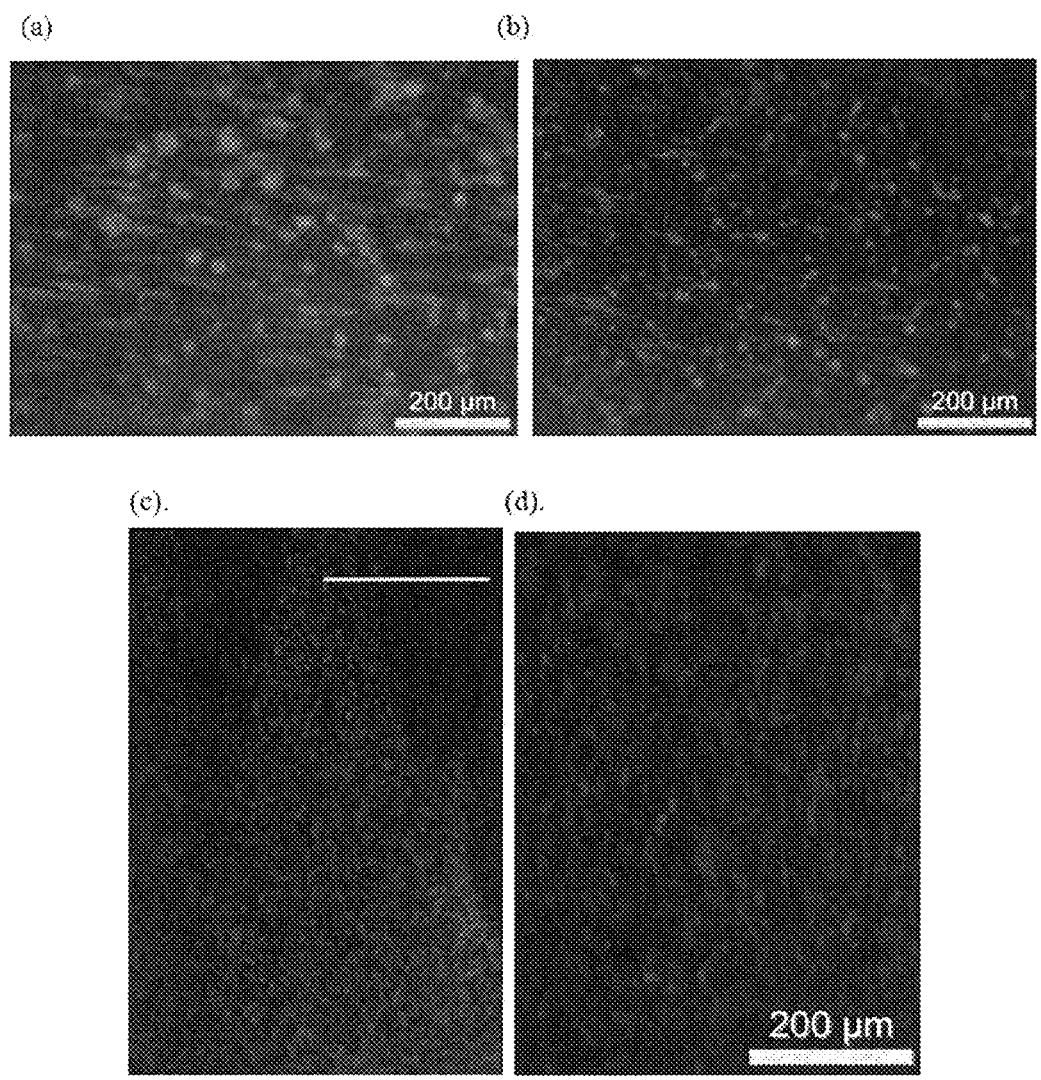
FIG. 20 shows VSMC seeding on the outside of gelatin coated PCL conduit tube. Without melt spun PCL fiber, the VSMC aligned along the length of the fiberless tube ((A) and (B)), however following the application of circumferentially aligned PCL melt spun fibers, the cells adopt circumferentially aligned orientation ((C) and (D)). For both sets of images are orientated with the longitudinal orientation shown horizontally. Scale bar in the figures denote a length of 200 µm.

Example 7: Application of Circumferentially Aligned Melt Spun Fibers onto Conduit Tube As shown in FIG. 19, decoration of the outer surface of the dip coated polymer tube with circumferentially aligned melt spun fibers along the entire length has been demonstrated. Prosthesis were fabricated with and without the aligned fibers then seeded with VSMC. From this experiment, it was found that without the aligning fibers the seeded VSMC orientated and spread horizontally along the length of the tube. Whereas with the inclusion of aligned fibers on the outer surface, the VSMC became aligned circumferentially, adopting the desired orientation for this construct (FIG. 20). Gelatin was used as a binder in this experiment rather than chitosan as it has better compliance with PLC than does chitosan, which becomes very stiff when dry.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for preparing a patterned substrate, the method comprising:
   a) melt-spinning at least one biocompatible polymer to form fibers;
   b) collecting the fibers on a substrate such that the fibers are aligned on the substrate; and
   c) applying a binding agent to the aligned fibers to bond the fibers into the aligned arrangement to obtain the patterned substrate in form of an aligned fiber mat.

2. The method according to claim 1, wherein collecting the fibers on a substrate comprises rotating the substrate such that the fibers are collected circumferentially around the substrate.

3. The method according to claim 1, wherein the substrate is a hollow tube comprising a biocompatible polymer.

4. The method according to claim 3, wherein the hollow tube is prepared by
   a) providing a cylindrical element having a first layer comprising a water-soluble polymer coated on a lateral surface of the cylindrical element;
   b) coating a second layer comprising a biocompatible polymer on the first layer;
   c) immersing the cylindrical element having the first and the second layer coated thereon in an aqueous solution to remove the first layer, and d) separating the second layer from the cylindrical element to obtain the hollow tube.

5. The method according to claim 4, wherein providing a cylindrical element having a first layer comprising a water-soluble polymer coated on a lateral surface of the cylindrical element comprises dip-coating the cylindrical element in a liquid reagent comprising the water-soluble polymer.

6. The method according to claim 4, wherein the water-soluble polymer comprises polyvinyl alcohol.

7. The method according to claim 4, wherein coating a second layer comprising a biocompatible polymer on the first layer comprises dip-coating the cylindrical element having the first layer coated thereon in a liquid reagent comprising the biocompatible polymer dissolved in an organic solvent.

8. The method according to claim 3, wherein an inner surface of the hollow tube is treated with an alkaline solution.

9. The method according to claim 8, wherein the inner surface of the hollow tube is further treated with at least one of gelatin and collagen.

10. The method according to claim 9, wherein the at least one of gelatin and collagen is immobilized on the inner surface of the hollow tube by carbodiimide crosslinking.

11. The method according to claim 3, wherein the hollow tube has a diameter in the range of about 2 mm to about 5 mm.

12. The method according to claim 1, wherein the biocompatible polymer is a biostable polymer or a biodegradable polymer.

13. The method according to claim 1, wherein the biocompatible polymer is selected from the group consisting of elastin, collagen, polyurethane, polycaprolactone, polylactide, polyglycolic acid, mixtures thereof, and copolymers thereof.

14. The method according to claim 1, wherein the binding agent is selected from the group consisting of gel-forming polysaccharides or proteins, polypeptides, alginate, glycosaminoglycans, hyaluronate, collagen, chitosan, gelatin, dopamine and mixtures thereof.

15. The method according to claim 1, wherein the biocompatible polymer of the fibers comprises a copolymer of polycaprolactone and polylactide, with the polylactide present in the range of about 50 wt % to about 80 wt % of the copolymer.

16. The method according to claim 1, wherein the binding agent is gelatin.

17. The method according to claim 1, wherein diameter of each fiber is about 10 μm.

18. A method for forming an implant for tissue engineering, the method comprising
   a) providing a patterned substrate prepared by a method comprising:
      i) melt-spinning at least one biocompatible polymer to form fibers;
      ii) collecting the fibers on a substrate such that the fibers are aligned on the substrate; and
      iii) applying a binding agent to the aligned fibers to bond the fibers into the aligned arrangement to obtain the patterned substrate in form of an aligned fiber mat;
   b) applying one or more species of living cells to the patterned substrate;
   c) incubating the patterned substrate comprising the one or more species of living cells under conditions which allow proliferation of the one or more species of living cells; and
   d) degrading the patterned substrate to obtain the implant.

19. The method according to claim 18, wherein the one or more species of living cells is selected from the group consisting of cardiomyocytes, induced progenitor cells, smooth muscle cells, fibroblasts, and mesenchymal stem cells.

20. The method according to claim 18, wherein the implant for tissue engineering forms at least part of a vascular prosthesis or a heart patch.

\* \* \* \* \*